(12) United States Patent
Asakura et al.

(10) Patent No.: US 10,408,762 B2
(45) Date of Patent: Sep. 10, 2019

(54) PLASMA PROCESSING APPARATUS, PLASMA PROCESSING METHOD AND PLASMA PROCESSING ANALYSIS METHOD

(71) Applicant: HITACHI HIGH-TECHNOLOGIES CORPORATION, Minato-ku, Tokyo (JP)

(72) Inventors: Ryoji Asakura, Tokyo (JP); Kenji Tamaki, Tokyo (JP); Daisuke Shiraishi, Tokyo (JP); Akira Kagoshima, Tokyo (JP); Satomi Inoue, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/825,098

(22) Filed: Aug. 12, 2015

(65) Prior Publication Data
US 2016/0225681 A1    Aug. 4, 2016

(30) Foreign Application Priority Data
Jan. 30, 2015    (JP) .................................. 2015-017642

(51) Int. Cl.
| H01L 21/66 | (2006.01) |
| H01L 21/67 | (2006.01) |

(Continued)

(52) U.S. Cl.
CPC .......... *G01N 21/68* (2013.01); *H01J 37/3299* (2013.01); *H01J 37/32926* (2013.01); *H01J 37/32972* (2013.01); *H01L 21/67253* (2013.01)

(58) Field of Classification Search
CPC ............... H01L 22/20; H01L 21/67253; H01L 21/67069; H01L 21/3065; G01N 21/68;
(Continued)

(56) References Cited

U.S. PATENT DOCUMENTS

| 5,170,367 A * | 12/1992 | Mackay ................. G01N 29/30 702/22 |
| 7,138,156 B1 * | 11/2006 | Myrick .................. G02B 5/285 359/359 |

(Continued)

FOREIGN PATENT DOCUMENTS

| JP | 2013-105923 A | 5/2013 |
| JP | 2013-161913 A | 8/2013 |

(Continued)

OTHER PUBLICATIONS

E. Sachs, et al. "Run by Run process control combinng SPC and feedback control", IEEE Transactions on Semiconductors Manufacturing, vol. 8, No. 1 (Feb. 1995), pp. 26-43.*

*Primary Examiner* — Caridad Everhart
(74) *Attorney, Agent, or Firm* — Miles & Stockbridge PC

(57) ABSTRACT

A plasma processing apparatus, plasma processing method, and plasma processing analysis method in which a suitable combination of wavelength, time interval, and etching condition parameter for control to change etching conditions is determined among wavelengths, time intervals, and changeable parameters for spectroscopic measurement data in order to ensure stable etching conditions. Specifically, a regression equation which represents the correlation between emission intensity and etching result at a wavelength and a time interval is obtained for each of two or more combinations of wavelength, time interval, and etching condition parameter. Furthermore, for each of the combinations, the amount of change is calculated from the regression equation when the value set for the etching condition parameter is changed. Among the combinations, the combination for which the amount of change is the smallest is determined as the combination of wavelength, time interval, and changed etching condition parameter to be used for control.

6 Claims, 16 Drawing Sheets

(51) Int. Cl.
*H01L 21/3065* (2006.01)
*G01N 21/68* (2006.01)
*H01J 37/32* (2006.01)

(58) Field of Classification Search
CPC ........... H01J 37/32972; H01J 37/32926; H01J 37/3299
See application file for complete search history.

(56) References Cited

U.S. PATENT DOCUMENTS

| | | | |
|---|---|---|---|
| 8,828,184 B2 | 9/2014 | Kagoshima et al. | |
| 2004/0045934 A1* | 3/2004 | Harvey | G01N 21/73 216/60 |
| 2005/0016947 A1* | 1/2005 | Fatke | H01J 37/32935 216/2 |
| 2005/0143952 A1* | 6/2005 | Tomoyasu | H01J 37/32935 702/181 |
| 2005/0146709 A1* | 7/2005 | Oh | H01J 37/32935 356/72 |
| 2007/0231930 A1* | 10/2007 | Funk | H01L 22/12 438/14 |
| 2009/0211706 A1 | 8/2009 | Uchida et al. | |
| 2012/0091097 A1* | 4/2012 | Chen | H01J 37/32926 216/59 |
| 2015/0004721 A1 | 1/2015 | Akimoto et al. | |
| 2015/0140692 A1* | 5/2015 | Tsai | H01L 22/12 438/14 |

FOREIGN PATENT DOCUMENTS

| | | |
|---|---|---|
| KR | 2009-092677 A | 9/2009 |
| KR | 2014-0119066 A | 10/2014 |

* cited by examiner

| MONITOR 1 | | MONITOR 2 | | CHANGED RECIPE PARAMETER |
|---|---|---|---|---|
| WAVELENGTH 1 | TIME INTERVAL 1 | WAVELENGTH 2 | TIME INTERVAL 2 | |
| 251 | 51-100 | 675 | 1-100 | GAS 1 FLOW RATE |

15a, 15b, 15c, 15d, 15e, 15f

RECIPE FIXED

RECIPE CHANGED (EXPERIMENTAL DATA)

RECIPE FIXED

RECIPE CHANGED (EXPERIMENTAL DATA)

FIG. 10

| | 23a | | | |
|---|---|---|---|---|
| WAFER ID | p1 | p2 | ... | p100 |
| ETCHING RESULT | 0.75 | 0.80 | ... | 1.04 |

23b → WAFER ID row; 23c → ETCHING RESULT row

| WAFER ID | p2 | | | |
|---|---|---|---|---|

| WAFER ID | p1 | | 24b | 24c |
|---|---|---|---|---|
| | | WAVELENGTH | | |
| | | 201 | 202 | ... | 800 |
| TIME | 1 | 103 | 103 | ... | 77 |
| | 2 | 107 | 108 | ... | 82 |
| | ... | ... | ... | ... | ... |
| | 100 | 140 | 142 | ... | 96 |

| | 25a | | | |
|---|---|---|---|---|
| WAFER ID | e1 | e2 | ... | e20 |
| ETCHING RESULT | 0.72 | 0.81 | ... | 0.63 |

25b → WAFER ID row; 25c → ETCHING RESULT row

F I G. 1 3

| | | e1 | e2 | ... | e20 |
|---|---|---|---|---|---|
| WAFER ID | | e1 | e2 | ... | e20 |
| AMOUNT OF RECIPE CHANGE | GAS 1 FLOW RATE | 10 | 20 | ... | 0 |
| | GAS 2 FLOW RATE | 0 | 0 | ... | 100 |

F I G. 1 4

| WAFER ID | e1 | | | | |
|---|---|---|---|---|---|
| | | WAVELENGTH | | | |
| | | 201 | 202 | ... | 800 |
| TIME | 1 | 121 | 125 | ... | 91 |
| | 2 | 123 | 126 | ... | 98 |
| | ... | ... | ... | ... | ... |
| | 100 | 154 | 158 | ... | 105 |

FIG. 15

| ID | APC SETUP CANDIDATES ||||| EVALUATION RESULT |||
| | MONITOR 1 || MONITOR 2 || CHANGED RECIPE PARAMETER | FIXED-RECIPE RESIDUAL | CHANGED-RECIPE RESIDUAL | MODEL DIFFERENCE | OVERALL EVALUATION |
| | WAVELENGTH 1 | TIME INTERVAL 1 | WAVELENGTH 2 | TIME INTERVAL 2 | | | | | |
|---|---|---|---|---|---|---|---|---|---|
| 1 | 201 | 51-100 | 201 | 1-100 | GAS 1 FLOW RATE | 0.024 | 0.027 | 0.073 | 0.124 |
| 2 | 211 | 51-100 | 201 | 1-100 | GAS 1 FLOW RATE | 0.025 | 0.026 | 0.039 | 0.09 |
| ⋮ | ⋮ | ⋮ | ⋮ | ⋮ | ⋮ | ⋮ | ⋮ | ⋮ | ⋮ |
| 100 | 251 | 51-1000 | 675 | 1-100 | GAS 1 FLOW RATE | 0.002 | 0.001 | 0.001 | 0.004 |
| ⋮ | ⋮ | ⋮ | ⋮ | ⋮ | ⋮ | ⋮ | ⋮ | ⋮ | ⋮ |
| 1001 | 201 | 51-100 | 201 | 1-100 | GAS 2 FLOW RATE | 0.033 | 0.038 | 0.021 | 0.097 |
| 1002 | 211 | 51-100 | 201 | 1-100 | GAS 2 FLOW RATE | 0.029 | 0.041 | 0.035 | 0.105 |
| ⋮ | ⋮ | ⋮ | ⋮ | ⋮ | ⋮ | ⋮ | ⋮ | ⋮ | ⋮ |

FIG. 18

| | 29a | | | |
|---|---|---|---|---|
| WAFER ID | p1 | p2 | ... | p100 |
| EMISSION INTENSITY MONITOR VALUE | 0.89 | 0.92 | ... | 0.95 |
| ETCHING RESULT | 0.75 | 0.80 | ... | 1.04 |

29b → WAFER ID
29c → EMISSION INTENSITY MONITOR VALUE
29d → ETCHING RESULT

FIG. 19

| | 29a-2a | | | |
|---|---|---|---|---|
| WAFER ID | e1 | e2 | ... | e10 |
| EMISSION INTENSITY MONITOR VALUE | 0.89 | 0.92 | ... | 0.95 |
| ETCHING RESULT | 0.72 | 0.81 | ... | 1.60 |

29-2b → WAFER ID
29-2c → EMISSION INTENSITY MONITOR VALUE
29-2d → ETCHING RESULT

F I G. 2 2 A
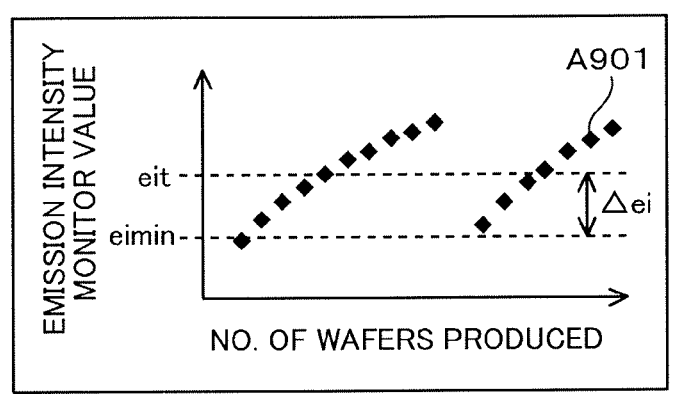
F I G. 2 2 B

PLASMA PROCESSING APPARATUS, PLASMA PROCESSING METHOD AND PLASMA PROCESSING ANALYSIS METHOD

BACKGROUND

The present invention relates to a plasma processing apparatus, plasma processing method, and plasma processing analysis method for processing a semiconductor wafer using a plasma.

In order to obtain a fine pattern for a semiconductor device, etc. formed on a wafer, etching may be performed using a substance in an ionized state (plasma state) to remove a substance on the wafer by action of the ionized substance (reaction on the wafer surface).

The width and depth of the semiconductor device fine pattern and the processing speed of an etching apparatus for the fine pattern (etch rate) will be hereinafter called "etching result". Due to various disturbances or change in the plasma state over time, it is difficult for the etching apparatus to achieve the same etching result even when processing is performed under the same etching conditions (hereinafter called "recipe"). For this reason, in order to stabilize the etching result, the etching apparatus adopts a control technique to change the recipe using apparatus monitor data obtained by measurement during etching (APC: Advanced Process Control). The monitor data is spectroscopic measurement data which is obtained by measuring the light emitted from the plasma during etching and the reflected light on the wafer surface by a spectroscope. The methods described in Japanese Unexamined Patent Application Publication No. 2013-105923 and Japanese Unexamined Patent Application Publication No. 2013-161913 are known as methods for adjusting the recipe using spectroscopic measurement data.

Japanese Unexamined Patent Application Publication No. 2013-105923 describes a method which uses, among apparatus monitor data including spectroscopic measurement data, a data parameter highly correlated with the etching result and adjusts the recipe based on the difference between the monitor data value and the target value for that data parameter.

Japanese Unexamined Patent Application Publication No. 2013-161913 describes a method which uses spectroscopic measurement data for data parameters highly correlated with the etching result (wavelength and time interval) among spectroscopic measurement data to estimate the etching result and adjusts the recipe using the estimation result.

SUMMARY

However, in both the methods described in Japanese Unexamined Patent Application Publication Nos. 2013-105923 and 2013-161913, the data parameters (wavelength and time interval for spectroscopic measurement data) to be used for APC are determined only according to the correlation between spectroscopic measurement data and etching result, and change in the correlation which is caused by change of the recipe is not taken into consideration. Since plasma light emission and the wafer surface condition change depending on the changed recipe parameter, the correlation between spectroscopic measurement data for the data parameters and the etching result may change. In APC, since change of the recipe is repeated using spectroscopic measurement data with a changed recipe, the correlation between spectroscopic measurement data with the data parameters used in APC and the etching result must be stabilized even with a changed recipe.

The present invention has an object to provide a plasma processing apparatus, plasma processing method, and plasma processing analysis method which determine a combination of a changed recipe parameter and data parameters (wavelength and time interval for spectroscopic measurement data) which ensures that change in the correlation is small even when the recipe is changed.

In order to achieve the above object, according to one aspect of the invention, there is provided a plasma processing apparatus which performs plasma processing on a specimen under APC as control to suppress fluctuations in plasma processing by feedback control or feedforward control and has an analysis unit to find a suitable combination for APC of emission wavelength, time interval for the emission wavelength, and a parameter (recipe) for plasma processing. The analysis unit obtains a first regression equation representing the correlation between emission intensity and plasma processing result, from temporal change data of the plasma processing, obtains a second regression equation representing the correlation between emission intensity and plasma processing result by changing the parameter, and finds a combination of wavelength, time interval for the wavelength, and a parameter for the plasma processing which is suitable for APC, based on a coefficient of correlation of the first regression equation, and a difference between a gradient of the first regression equation and a gradient of the second regression equation.

In order to achieve the above object, according to a second aspect of the invention, there is provided a plasma processing apparatus which performs plasma processing on a specimen under APC as control to suppress fluctuations in plasma processing by feedback control or feedforward control and is connected with an analysis unit configured to select a suitable combination for APC of emission wavelength, time interval for the emission wavelength, and a parameter for the plasma processing. The analysis unit obtains a first regression equation representing the correlation between emission intensity and plasma processing result, from temporal change data of the plasma processing, obtains a second regression equation representing the correlation between emission intensity and plasma processing result by changing the parameter, and finds a combination of wavelength, time interval for the wavelength, and a parameter for the plasma processing which is suitable for APC, based on a coefficient of correlation of the first regression equation, and a difference between a gradient of the first regression equation and a gradient of the second regression equation.

In order to achieve the above object, according to a third aspect of the invention, there is provided a plasma processing method using a plasma processing apparatus which performs plasma processing on a specimen under APC as control to suppress fluctuations in plasma processing by feedback control or feedforward control and has an analysis unit to find a suitable combination for APC of emission wavelength, time interval for the emission wavelength, and a parameter for the plasma processing. The method includes the steps of: obtaining a first regression equation representing the correlation between emission intensity and plasma processing result from temporal change data of the plasma processing by using the analysis unit; obtaining a second regression equation representing the correlation between emission intensity and plasma processing result by changing the parameter by using the analysis unit; finding a combination of wavelength, time interval for the wavelength, and a parameter for the plasma processing which is suitable for APC, based on a coefficient of correlation of the first regression equation, and a difference between a gradient of the first regression equation and a gradient of the second regression equation by using the analysis unit; and performing plasma processing by using the plasma processing apparatus on the specimen under APC which uses the combination of wavelength, time interval for the wavelength, and a parameter for the plasma processing as found by the analysis unit.

In order to achieve the above object, according to a fourth aspect of the invention, there is provided an analysis unit which finds a combination of wavelength, time interval for the wavelength, and a parameter for plasma processing which is suitable for control to suppress fluctuations in the plasma processing by feedback control or feedforward control. In the analysis unit, a first regression equation representing the correlation between emission intensity and plasma processing result is obtained from temporal change data of the plasma processing; a second regression equation representing the correlation between emission intensity and plasma processing result is obtained by changing the parameter; and a combination of wavelength, time interval for the wavelength, and a parameter for the plasma processing which is suitable for the control is found based on a coefficient of correlation of the first regression equation, and a difference between a gradient of the first regression equation and a gradient of the second regression equation.

Furthermore, in order to achieve the above object, according to a fifth aspect of the invention, there is provided an analysis method which finds a combination of wavelength, time interval for the wavelength, and a parameter for plasma processing which is suitable for control to suppress fluctuations in the plasma processing by feedback control or feedforward control. The method includes the steps of: obtaining a first regression equation representing the correlation between emission intensity and plasma processing result from temporal change data of the plasma processing; obtaining a second regression equation representing the correlation between emission intensity and plasma processing result by changing the parameter; and finding a combination of wavelength, time interval for the wavelength, and a parameter for the plasma processing which is suitable for the control, based on a coefficient of correlation of the first regression equation, and a difference between a gradient of the first regression equation and a gradient of the second regression equation.

According to the present invention, it is possible to determine a combination of wavelength and time interval and a changed recipe parameter for spectroscopic measurement data which ensures that change in the correlation between spectroscopic measurement data and etching result is small even when the recipe is changed, so that etching results are stabilized.

These features and advantages of the invention will be apparent from the following more particular description of preferred embodiments of the invention, as illustrated in the accompanying drawings.

BRIEF DESCRIPTION OF THE DRAWINGS

FIG. 10 shows an example of a fixed-recipe etching result data table according to an embodiment of the present invention;

FIG. 11 shows an example of a fixed-recipe spectroscopic measurement data table according to an embodiment of the present invention;

FIG. 12 shows an example of a changed-recipe etching result data table according to an embodiment of the present invention;

FIG. 13 shows an example of a changed-recipe recipe data table according to an embodiment of the present invention;

FIG. 14 shows an example of a changed-recipe spectroscopic measurement data table according to an embodiment of the present invention;

FIG. 15 shows an example of an APC setup data candidate table according to an embodiment of the present invention;

FIG. 18 shows an example of an emission intensity monitor value data table according to an embodiment of the present invention;

FIG. 19 shows an example of an emission intensity monitor value data table in which data with a changed recipe is stored;

FIG. 22A is a diagram showing an example of change in emission intensity monitor value with a fixed recipe;

FIG. 22B is a diagram showing an example of change in etching result with a fixed recipe;

DETAILED DESCRIPTION OF THE PREFERRED EMBODIMENTS

Figure 1:
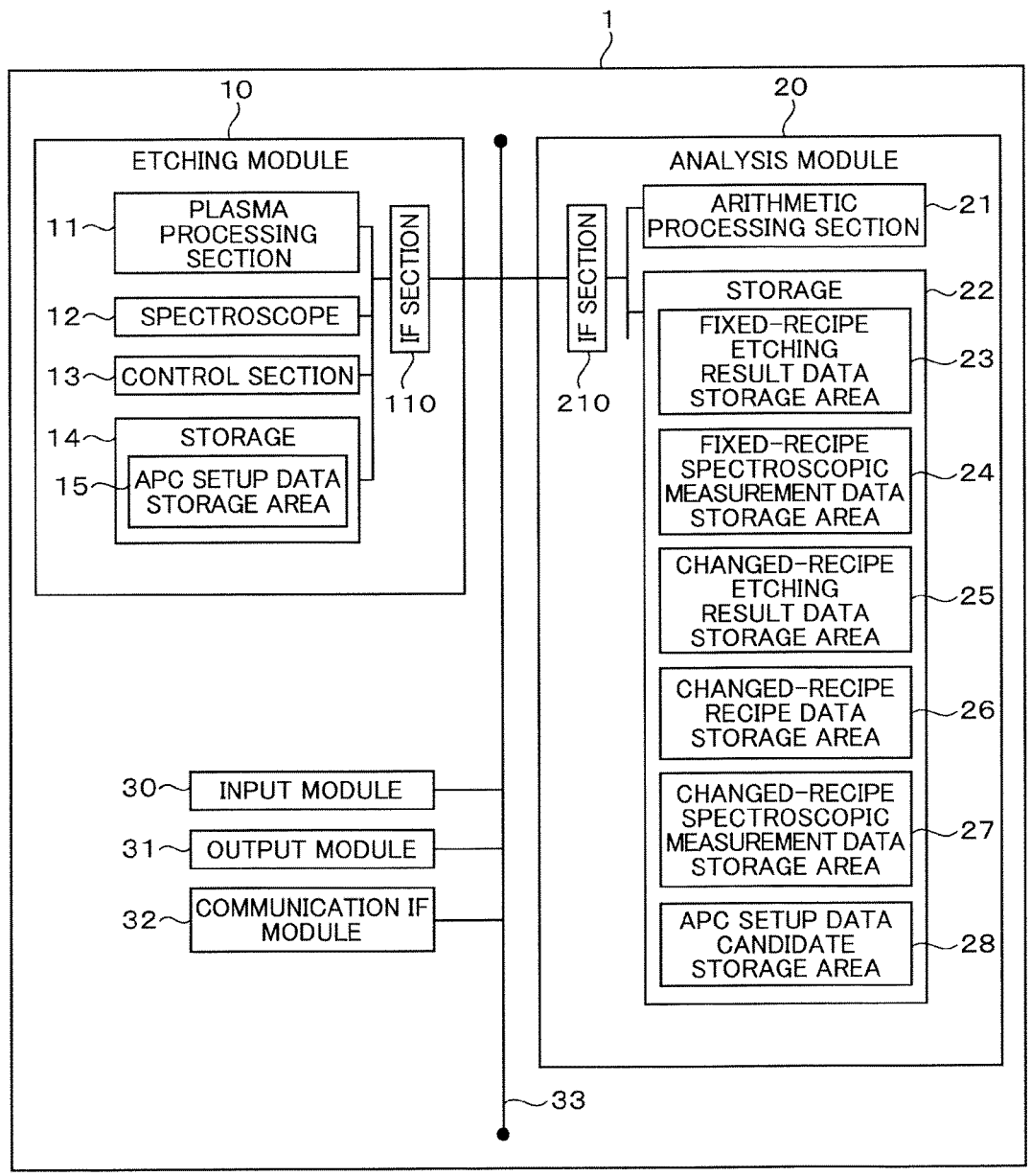
FIG. 1 is a block diagram showing the general configuration of an etching apparatus according to an embodiment of the present invention.

The present invention concerns a plasma processing apparatus, plasma processing method, and plasma processing analysis method for performing etching, in which spectroscopic measurement data indicating emission intensity at different wavelengths and times in the etching process and the etching result are acquired, and as for different combinations of wavelength and time interval for spectroscopic measurement data and a changeable recipe parameter, comparison is made between the regression equation between average emission intensity and etching result with a fixed recipe and the regression equation between average emission intensity and etching result with a changed recipe for each combination of wavelength and time interval, and the combination of wavelength, time interval, and a changed recipe parameter for spectroscopic measurement data to be used for APC is determined based on the difference between the coefficients of the two regression equations. The combination thus determined is applied to the plasma processing method and plasma processing apparatus for etching or the like.

Specifically, according to the present invention, in the plasma processing apparatus, plasma processing method, and plasma processing analysis method, the following processes (1) to (3) are carried out:
(1) Combinations of wavelength indicating the emission wavelength band of spectroscopic measurement data obtained by a spectroscope, time interval indicating the time when the spectroscopic measurement data is obtained, and the recipe parameter to be changed are created.
(2) As for each of the combinations of wavelength, time interval and changed recipe thus created, using the data with a fixed recipe, regression equation 1 representing the correlation between spectroscopic measurement data at the relevant wavelength and time interval and the etching result and regression equation 2 representing the correlation between spectroscopic measurement data at the relevant wavelength and time interval and the etching result with a changed recipe parameter are created.
(3) As for each of the combinations of wavelength, time interval and changed recipe parameter, the difference between the coefficient of the regression equation 1 and the coefficient of the regression equation 2 is calculated, and among the combinations, the combination for which the difference is small is presented as the combination of wavelength, time interval and changed recipe parameter to be used for APC.

In order to solve the above problem, according to the present invention, in the plasma processing method for etching, the above processes (1) to (3) are carried out and using the wavelength and time interval in the above-determined combination of wavelength, time interval and changed recipe parameter, an emission intensity monitor value as spectroscopic measurement data at the wavelength and time interval is calculated and the value of the changed recipe parameter determined in the above processes is changed according to the difference between the calculated emission intensity monitor value and the target emission intensity monitor value.

Furthermore, in order to solve the above problem, according to the present invention, in the plasma processing apparatus which performs etching, the above processes (1) to (3) are carried out, and using the wavelength and time interval in the above-determined combination of wavelength, time interval and changed recipe parameter, an emission intensity monitor value as spectroscopic measurement data at the wavelength and time interval is calculated and the value of the changed recipe parameter determined in the above processes is changed according to the difference between the calculated emission intensity monitor value and the target emission intensity monitor value.

Next, the preferred embodiments of the present invention will be described referring to the accompanying drawings. In all the drawings that illustrate the preferred embodiments, basically the same members are designated by the same reference signs and descriptions thereof are not repeated.

Etching Apparatus

As an example of a plasma processing apparatus according to an embodiment of the invention, an etching apparatus will be described below. As shown in the block diagram of FIG. 1, the etching apparatus 1 in this embodiment includes an etching module 10, an analysis module 20, an input module 30, an output module 31, and a communication interface module (communication IF module) 32 which are interconnected through a bus 33.

The etching module 10 includes a plasma processing section 11, a spectroscope 12, a control section 13, a storage 14, and an interface section (IF section) 110. The plasma processing section 11 generates plasma to process a wafer and the spectroscope 12 acquires spectroscopic measurement data including plasma light emission data and reflected light on the wafer surface while etching is under way. The spectroscopic measurement data is stored in the storage 22 of the analysis module 20 through the IF sections 110 and 210. The control section 13 controls processing which is performed in the plasma processing section 11. The storage 14 has an APC setup data storage area 15 which stores the wavelength, time interval and changed recipe parameter to be used for control (APC) by the control section 13 to change the recipe. Details of the etching module 10 will be given later, referring to FIG. 2. Also, the APC process by the control section 13 will be described in detail later.

The analysis module 20 performs processing to determine the combination of wavelength, time interval, and changed recipe parameter which is used for APC as control to suppress fluctuations in plasma processing by feedback control or feedforward control. The analysis module 20 includes an arithmetic processing section 21 for data analysis, a storage 22, and an interface section (IF section) 210.

The storage 22 includes a fixed-recipe etching result data storage area 23 for storing results of etching with a fixed recipe, a fixed-recipe spectroscopic measurement data storage area 24 for storing spectroscopic measurement data obtained during an etching process with a fixed recipe, a changed-recipe etching result data storage area 25 for storing results of etching with a changed recipe, a changed-recipe recipe data storage area 26 for storing recipe setting values in an etching process with a changed recipe, a changed-recipe spectroscopic measurement data storage area 27 for storing spectroscopic measurement data obtained during an etching process with a changed recipe, and an APC setup data candidate storage area 28 for storing candidates for the combination of wavelength, time interval, and changed recipe parameter to be used for APC, and evaluation results thereof.

The arithmetic processing section 21 compares the regression equation between emission intensity and etching result with a fixed recipe with the regression equation between emission intensity and etching result with a changed recipe for each combination of wavelength, time interval, and changed recipe parameter, using the etching result data stored in the fixed-recipe etching result data storage area 23 of the storage 22, the spectroscopic measurement data stored in the fixed-recipe spectroscopic measurement data storage area 24, the etching result data stored in the changed-recipe etching result data storage area 25, and the spectroscopic measurement data stored in the changed-recipe spectroscopic measurement data storage area 27, and performs processing to determine the combination of wavelength, time interval, and changed recipe parameter to be used in APC, based on the difference in coefficient between the two regression equations. The analysis processing by the arithmetic processing section 21 will be described in detail later.

The input module 30 includes devices to receive information entered by a user, such as a mouse and a keyboard. The output module 31 includes devices to output information to the user, such as a display and a printer. The communication IF module 32 is an interface which is connected to another apparatus (connectable to an inspection device for measuring the etching result, etc.) or system (connectable to an existing production management system, etc.) through the bus 33 or an external network, etc. to transmit and receive information. The bus 33 interconnects the various modules (10, 20, 30, 31, 32). The IF sections (110, 210, etc.) are interfaces to transmit and receive information through the bus 33. The analysis module 20 may be an independent analysis unit which is connected to the etching apparatus including the etching section 10 through the IF section 210.

Etching Module

Figure 2:
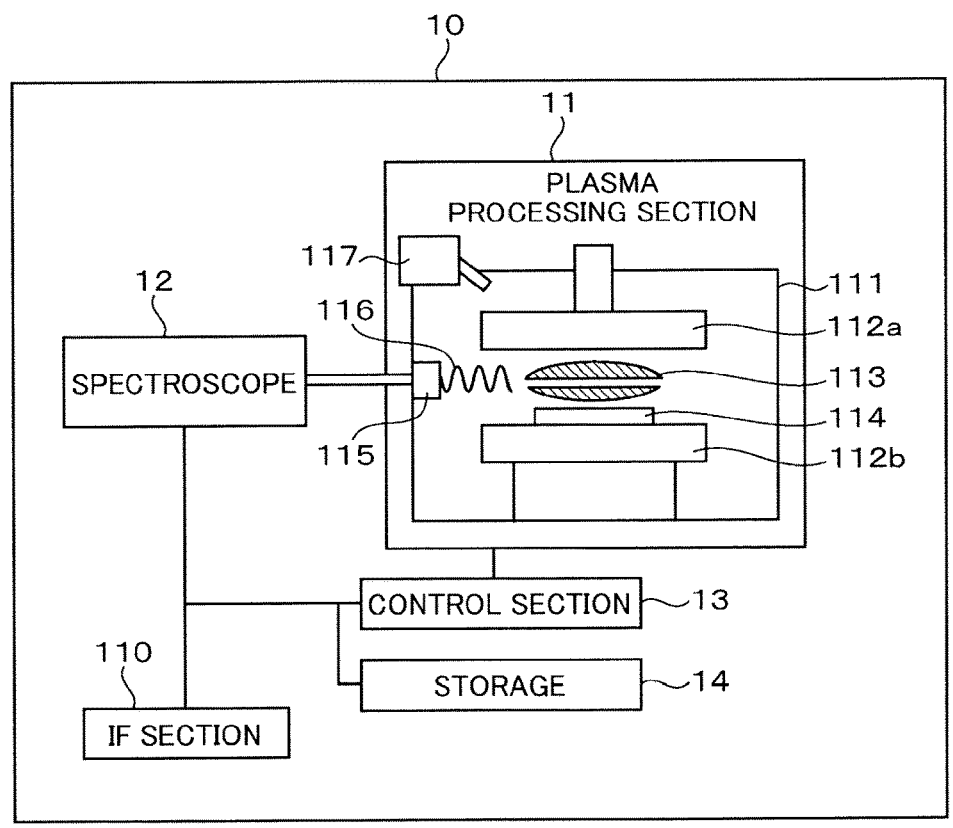
FIG. 2 is a block diagram showing the general configuration of the etching module of the etching apparatus according to an embodiment of the present invention.

The etching module 10 includes a plasma processing section 11, a spectroscope 12, a control section 13, a storage 14, and an IF section 110. As shown in FIG. 2, the plasma processing section 11 includes a chamber 111 the inside of which is air-evacuated by a vacuum exhaust means (not shown), a pair of electrodes 112a and 112b which generates a plasma in the air-evacuated chamber 111 supplied with radio frequency power from a power source (not shown), a window 115 for observing the inside of the chamber 111 from outside, and a gas supply section 117 for supplying etching gas for etching a wafer 114 into the air-evacuated chamber 111. The gas supply section 117 can supply several types of gas (CF4, CHF3, Ar, etc.), in which the flow rate of each type of gas is controlled.

In this structure, according to a command from the control section 13, the plasma processing section 11 is supplied with etching gas from the gas supply section 117 while the wafer 114 is set inside the chamber 111 and the inside of the chamber 111 is air-evacuated by the exhaust means (not shown). Then, the etching gas is supplied into the chamber 111 and a radio frequency discharge is generated between the electrodes 112a and 112b by applying radio frequency power from the power source (not shown) to the electrodes 112a and 112b to generate plasma. The wafer 114 is processed by collision of the plasma gas 113 against the wafer 114.

The plasma gas 113 contains elements of the etching gas supplied from the gas supply section 117 and elements generated during processing of the wafer 114 and generates light 116 with wavelength corresponding to the elements contained in the plasma gas 113. The generated light 116 is measured by the spectroscope 12 through the window 115. And the measured data is stored in the fixed-recipe spectroscopic measurement data storage area 24 of the storage 22 of the analysis module 20 through the IF section 110. Alternatively, an external light source (not shown) may be used to irradiate the wall surface of the chamber 111 and the wafer 114 with light so that the reflected light is measured by the spectroscope 12.

The control section 13 gives commands to the plasma processing section 11 and receives spectroscopic measurement data obtained by the spectroscope 12 and performs processing to change the recipe as described later in recipe change control (Advanced Process control: APC).

The APC setup data storage area 15 of the storage 14 stores data which the control section 13 uses for APC.

Figures 4, 5:
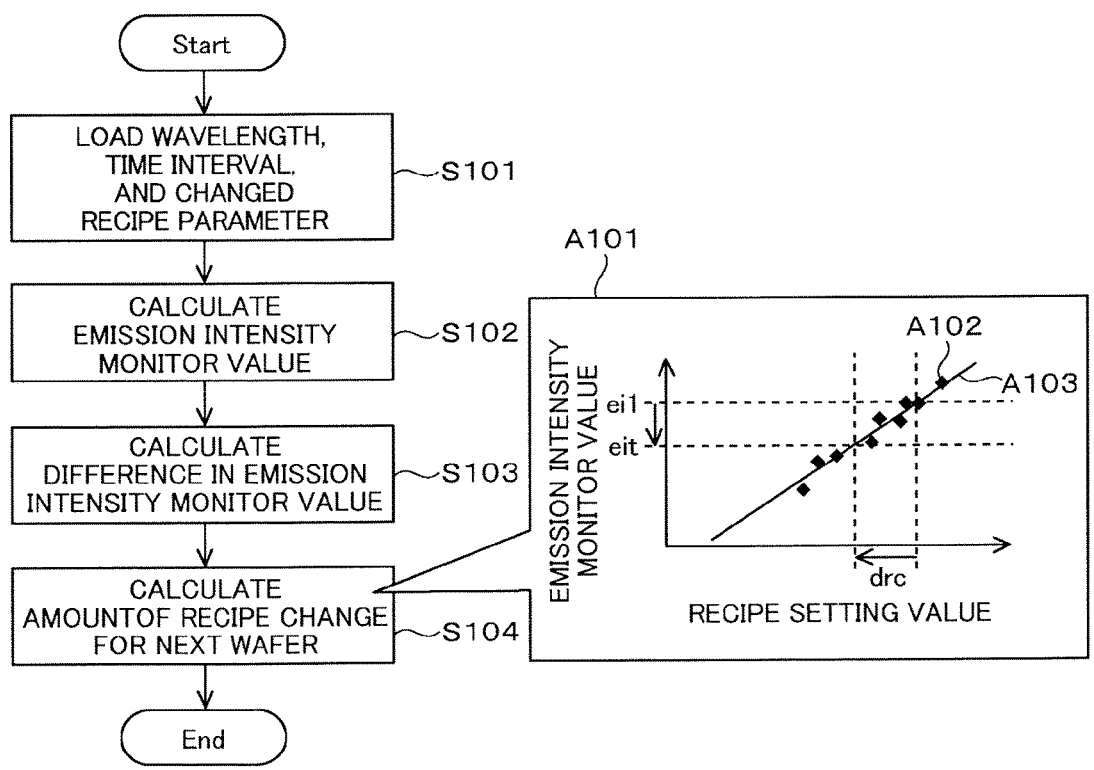
FIG. 4 shows an example of an APC setup data table according to an embodiment of the present invention.
FIG. 5 is a flowchart for explaining an example of control (APC) in which the recipe is changed.

FIG. 4 shows an APC setup data table 15a as an example of the APC setup data storage area 15. The table contains a wavelength 1 field 15b, a time interval 1 field 15c, a wavelength 2 field 15d, a time interval 2 field 15e, and a changed recipe parameter field 15f.

The wavelength 1 field 15b stores information to identify the wavelength for spectroscopic measurement data to calculate the average emission intensity.

The time interval 1 field 15c stores information to identify the time interval for spectroscopic measurement data to calculate the average emission intensity.

The wavelength 2 field 15d stores information to identify the wavelength for spectroscopic measurement data to calculate the average emission intensity.

The time interval 2 field 15e stores information to identify the time interval for spectroscopic measurement data to calculate the average emission intensity.

The changed recipe parameter field 15f stores information to identify the recipe parameter (gas flow rate, etc.) to be changed in APC.

After etching is finished, the processed wafer 114 is taken out from the chamber 111 and transported to another device (inspection device or the like), and then another wafer 114 is set in the etching module 10 and the wafer 114 is processed by etching. The processed wafer 114 is measured in another device (inspection device or the like) to obtain pattern dimensions as the result of etching. The measured pattern dimensions are stored in the etching result data storage area 23 of the storage 22 as etching result data.

Spectroscopic Measurement Data

Figure 3:
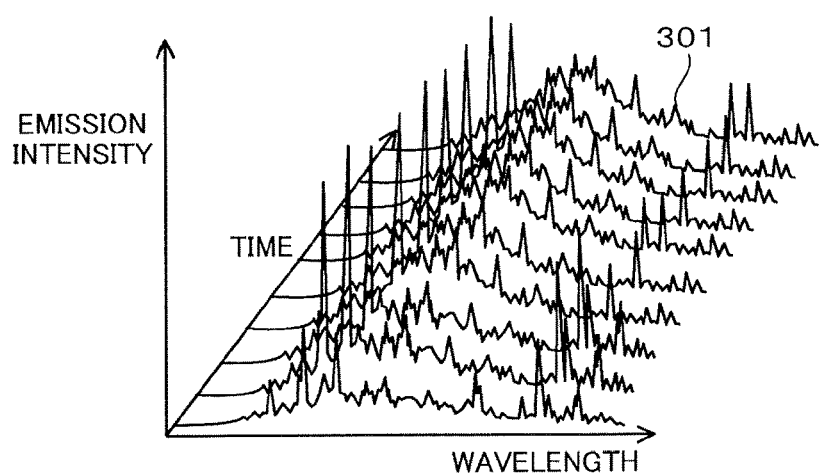
FIG. 3 is a graph for explaining an example of spectroscopic measurement data.

FIG. 3 shows a waveform signal 301 as an example of spectroscopic measurement data of plasma emission measured by the spectroscope 12. The waveform signal 301 as spectroscopic measurement data has two-dimensional factors, wavelength and time, and represents the value of emission intensity measured at each wavelength and each time. The value of emission intensity at each wavelength and each time is stored in the spectroscopic measurement data storage area 24 (described later) together with the ID of the wafer corresponding to the spectroscopic measurement data.

Recipe Change Control (APC)

FIG. 5 shows an example of APC processing which is performed in the control section 13.

When the execution of APC is programmed, upon completion of wafer etching the control section 13 loads the information on wavelength, time interval, and changed recipe parameter stored in the APC setup data storage area 15 of the storage 14 (S101). In an example of APC processing, a plurality of wafers are processed sequentially using the wavelength, time interval, and changed recipe parameter stored in the APC setup data storage area 15, except for the first wafer for which the preset conditions are used.

Next, the following calculation is made (S102): the average emission intensity calculated from the waveform signal 301 stored in the fixed-recipe spectroscopic measurement data storage area 24 based on the combination of wavelength and time interval stored in the spectroscopic measurement data wavelength 1 field 15*b* and time interval 1 field 15*c* of the APC setup data table 15*a* is divided by the average emission intensity calculated from the waveform signal 301 stored in the fixed-recipe spectroscopic measurement data storage area 24 based on the combination of wavelength and time interval stored in the spectroscopic measurement data wavelength 2 field 15*d* and time interval 2 field 15*e*. The result of dividing the average emission intensity by the other average emission intensity as mentioned above will be hereinafter called an emission intensity monitor value. Alternatively the average emission intensity calculated from the waveform signal 301 stored in the fixed-recipe spectroscopic measurement data storage area 24 based on the combination of wavelength and time interval stored in the wavelength 1 field 15*b* and time interval 1 field 15*c* may be directly taken as an emission intensity monitor value. Furthermore, the maximum or median value of emission intensity extracted from the waveform signal 301 stored in the fixed-recipe spectroscopic measurement data storage area 24 based on the combination of wavelength and time interval stored in the wavelength 1 field 15*b* and time interval 1 field 15*c* may be taken as an emission intensity monitor value.

Next, the control section 13 calculates the difference between the emission intensity monitor value calculated at S102 and the target emission intensity monitor value preset by the apparatus manager is calculated (S103).

Furthermore, the control section 13 calculates the amount of recipe change, for example, the flow rate of etching gas supplied from the gas supply section 117 (gas flow rate) according to the difference between the emission intensity monitor value calculated at S103 and the target emission intensity monitor value (S104). The recipe parameter which is changed here is the recipe parameter stored in the changed recipe parameter field 15*f*.

The graph A101 on the right in FIG. 5 shows an example of calculation of the amount of recipe change which is made at S104. A101 is a scatter diagram in which the value of each wafer (A102) is plotted on the horizontal axis representing the recipe setting value and the vertical axis representing the emission intensity monitor value. The example shown in A101 reveals that the recipe setting value and the emission intensity monitor value are correlated. Line A103 is a regression line which represents the relation between the emission intensity monitor values obtained from a plurality of points A102 and the recipe setting value. For example, the line A103 is drawn so that the sum of squares of the distance from each of the points A102 is minimum. In the graph A101, ei1 denotes the emission intensity monitor value calculated at S102 and eit denotes the target emission intensity monitor value.

At the step of S104, the amount of recipe change (drc) for the recipe parameter stored in the changed-recipe parameter field 15*f* is calculated from the difference between the emission intensity monitor value (ei1) and the target emission intensity monitor value (eit) using the regression line A103 as indicated by dotted lines. The control section 13 changes the recipe by the amount of recipe change calculated here for etching the next wafer. As a result of this recipe change, the emission intensity monitor value becomes closer to the target emission intensity monitor value (eit).

Next, an example of control of the emission intensity monitor value and etching result will be described referring to FIG. 6, FIG. 7A, and FIG. 7B.

Figure 6:
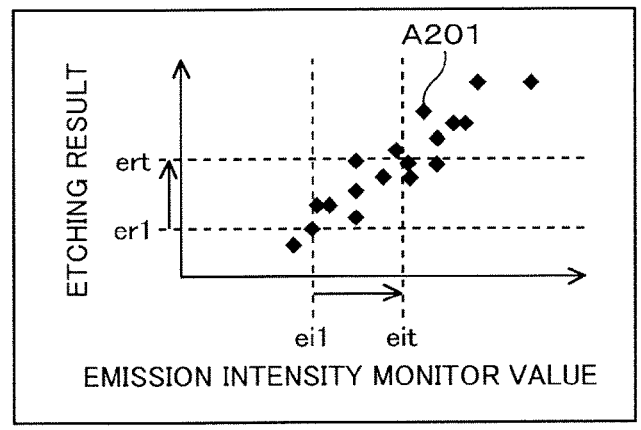
FIG. 6 is a scatter diagram showing an example of the correlation between emission intensity monitor value and etching result.

FIG. 6 is a scatter diagram in which the value of each wafer (A201) is plotted on the horizontal axis representing the emission intensity monitor value and the vertical axis representing the etching result. As shown in the diagram, when the emission intensity monitor value and etching result are correlated, the etching result (for example, er1) can be made closer to the target value (ert) by controlling the emission intensity monitor value (for example, ei1) to make it closer to the target value (eit). Taking advantage of this feature, even if the emission intensity monitor value or etching result deviates from the target value due to temporal change or disturbance, the etching result can be made closer to the target value (ert) by executing APC so as to make the emission intensity monitor value closer to the target value (eit).

Figure 7A:
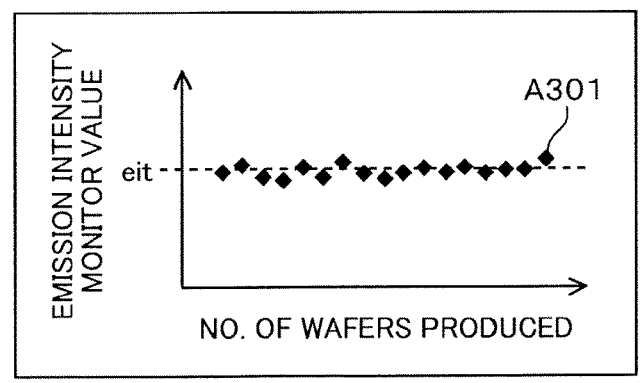
FIG. 7A is a diagram showing an example of change in emission intensity monitor value when APC is executed.
Figure 7B:
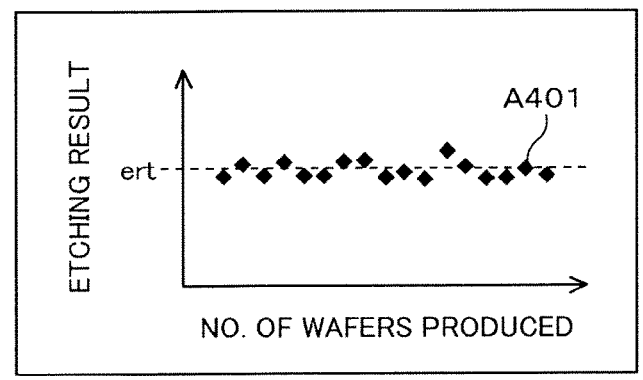
FIG. 7B is a diagram showing an example of change in etching result when APC is executed.

FIGS. 7A and 7B show changes in emission intensity monitor value and etching result when etching is performed under APC, respectively. Points (A301, A401) in FIGS. 7A and 7B represent the emission intensity monitor value and etching result for each etched wafer respectively and from the figures, it is known that the points converge around the target values (eit, ert).

However, if the correlation between change in emission intensity monitor value and change in etching result with a fixed recipe, attributable to temporal change, is different in tendency from the correlation between change in emission intensity monitor value and change in etching result with a changed recipe, attributable to recipe change, it may be difficult to perform control so that the points representing the etching result converge around the target value. The reason will be explained below referring to FIGS. 8A and 8B.

Figure 8A:
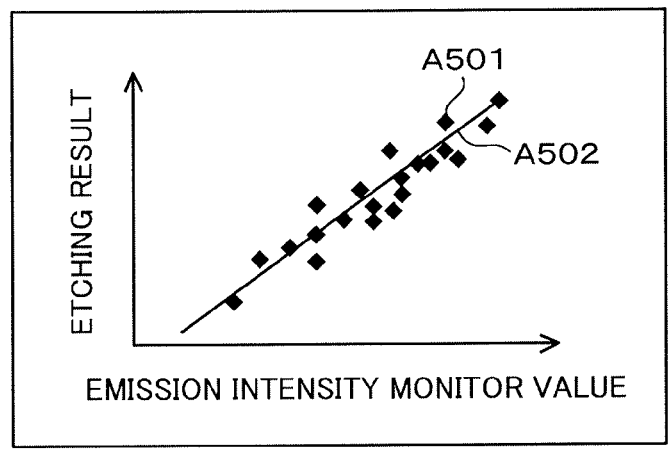
FIG. 8A is a scatter diagram showing an example of the correlation between emission intensity monitor value and etching result when the recipe is fixed.

FIG. 8A is a scatter diagram in which the value of each wafer (A501) is plotted on the horizontal axis representing the emission intensity monitor value and the vertical axis representing the etching result when the recipe is fixed. FIG. 22A (to which reference will be made later) is a diagram in which the emission intensity monitor value with a fixed recipe is plotted for each wafer. The figure suggests that the emission intensity monitor value changes over time. FIG. 22B plots the etching result with a fixed recipe for each wafer. It also suggests temporal change. FIG. 8A indicates the relation between emission intensity monitor value and etching result when temporal change occurs as shown in FIGS. 22A and 22B. Line A502 is a regression line which expresses the correlation between the emission intensity monitor values obtained from a plurality of points A501 and the etching result. For example, the line A502 is drawn so that the sum of squares of distance from each of the points A501 is minimum.

Figure 8B:
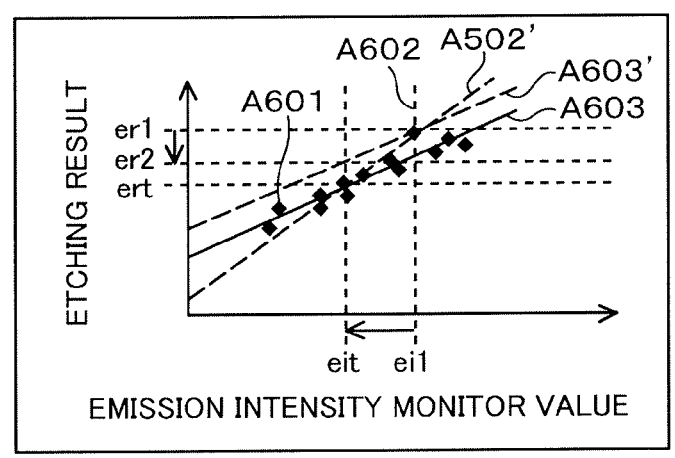
FIG. 8B is a scatter diagram showing an example of the correlation between emission intensity monitor value and etching result when the recipe is changed.

FIG. 8B is a scatter diagram in which the value of each wafer (A601) is plotted on the horizontal axis representing the emission intensity monitor value and the vertical axis representing the etching result when the recipe is changed. FIG. 8B is created from data collected by experiments before execution of APC. The figure indicates the relation between the emission intensity monitor value and etching result which have changed due to recipe change, in which line A603 is a regression line which expresses the correlation between emission intensity monitor value and etching result by the change of recipe. A602 represents the target emission intensity monitor value (eit) and the target etching result (ert). Line A502' represents the regression line (A502)

with a fixed recipe as explained above in reference to FIG. 8A, which is included in this scatter diagram.

Figure 9A:
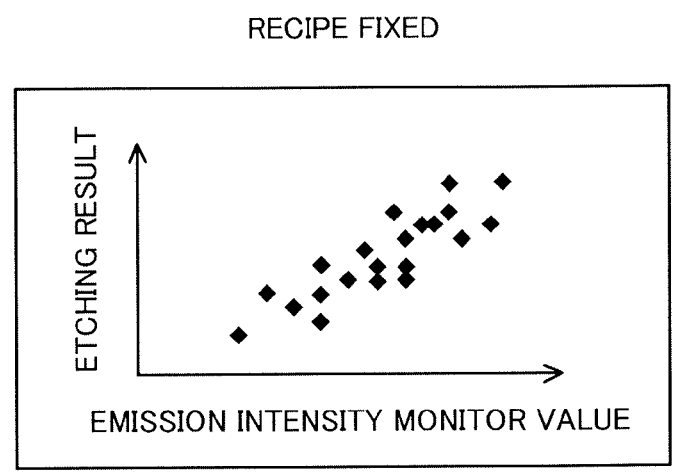
FIG. 9A is a scatter diagram showing an example of the correlation between emission intensity monitor value and etching result when the recipe is fixed, in which the difference between the correlation with the fixed recipe and the correlation with the changed recipe is small.
Figure 9B:
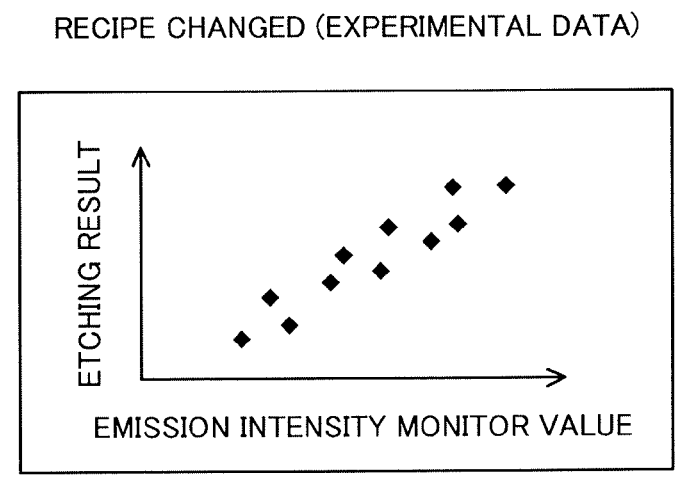
FIG. 9B is a scatter diagram showing the correlation between emission intensity monitor value and etching result when the recipe is changed, in which the difference between the correlation with the fixed recipe and the correlation with the changed recipe is small.

When the emission intensity monitor value and etching result with a fixed recipe change to ei1 and er1 due to temporal change respectively, if the recipe is changed so as to make the emission intensity monitor value (ei1) equal to the target value (eit), the etching result (er1) changes as indicated by line A603' parallel to line A603 and the etching result under control becomes er2. When the difference between the gradients of the lines A603' and A502' is smaller, the difference between the target etching result value (ert) and the etching result (er2) at the emission intensity monitor value equal to the target value is smaller. Therefore, when APC is executed, it is necessary to ensure that the correlation between emission intensity monitor value and etching result with a fixed recipe has the same gradient as that with a changed recipe (the regression lines have the same gradient) as shown in FIGS. 9A and 9B.

The effectiveness of APC in making the emission intensity constant has been explained so far. However, even when control to make the emission intensity constant is not performed but the etching result is estimated using emission intensity data and the recipe is controlled according to the estimated etching result, it is desirable that the difference between the gradient of the regression line (A502) representing the correlation between emission intensity monitor value and etching result with a fixed recipe and the gradient of the regression line (A603) representing the correlation between emission intensity monitor value and etching result with a changed recipe be small. This is because when the difference in gradient and intercept between the two regression lines is small, the etching result can be estimated using the same regression line when the recipe is fixed as when the recipe is changed, and the etching result can be estimated stably with a smaller amount of calculation.

Analysis Module

The information about the etching performed without changing a predetermined standard recipe is stored in the fixed-recipe etching result data storage area 23 and fixed-recipe spectroscopic measurement data storage area 24 of the storage 22 shown in FIG. 1.

FIG. 10 shows a fixed-recipe etching result data table 23a as an example of the fixed-recipe etching result data storage area 23. The table includes a wafer ID field 23b and an etching result field 23c.

The wafer ID field 23b stores information which identifies the wafer 114. The value stored in the wafer ID field 23b is associated with the value stored in the wafer ID field 24b of the spectroscopic measurement data table 24a (described later) so that the spectroscopic measurement data obtained during etching of each wafer is associated with the etching result.

The etching result field 23c stores information which identifies the etching result. For example, it stores the result of surface pattern measurement of the etched wafer 114 identified in the wafer ID field 23b measured by an inspection device connected to the etching apparatus 1 (for example, the dimensions of patterns formed on the wafer 114 and inter-pattern distances as measured by a measuring SEM). For each wafer, the surface pattern dimensional information is stored in the etching result data storage area 23 through the communication IF module 32.

FIG. 11 shows a fixed-recipe spectroscopic measurement data table 24a as an example of the fixed-recipe spectroscopic measurement data storage area 24. The table includes a wafer ID field 24b, a wavelength field 24c, a time field 24d, and an emission intensity value field 24e. This table is provided in the same number as the number of wafers.

The wafer ID field 24b stores information which identifies the wafer 114. The value stored in the wafer ID field 24b is associated with the value stored in the wafer ID field 23b of the fixed-recipe etching result data table 23a described above in reference to FIG. 10.

The emission intensity value field 24e stores measured emission intensity values at wavelengths in the wavelength field 24c and at times in the time field 24d.

The changed-recipe etching result data storage area 25, changed-recipe recipe data storage area 26, and changed-recipe spectroscopic measurement data storage area 27 of the storage 22 shown in FIG. 1 store information about etching performed with the predetermined standard recipe partially changed.

FIG. 12 shows a changed-recipe etching result data table 25a as an example of the changed-recipe etching result data storage area 25. The table includes a wafer ID field 25b and an etching result field 25c.

The wafer ID field 25b stores information which identifies the wafer 114. The value stored in the wafer ID field 25b is associated with the value stored in the wafer ID field 26b of the changed-recipe recipe data table 26a (described later) and the value stored in the wafer ID field 27b of the spectroscopic measurement data table 27a (described later) so that the amount of recipe change used for etching each wafer is associated with the spectroscopic measurement data and etching result obtained by etching.

The etching result field 25c stores information which identifies the etching result. For example, it stores the result of surface pattern measurement of the etched wafer 114 identified in the wafer ID field 25b measured by an inspection device connected to the etching apparatus 1 (for example, the dimensions of patterns formed on the wafer 114 and inter-pattern distances as measured by a measuring SEM). The information stored here is the result of measurement of a spot on the wafer as information which is the same as or comparable to the information in the etching result field 23c of the fixed-recipe etching result data table 23a. For example, if the etching result field 23c stores the inter-pattern distance in the center of the wafer, the etching result field 25c also stores the inter-pattern distance in the center of the wafer.

FIG. 13 shows a changed-recipe recipe data table 26a as an example of the changed-recipe recipe data storage area 26. The table includes a wafer ID field 26b and a recipe change amount field 26c.

The wafer ID field 26b stores information which identifies the wafer 114. The value stored in the wafer ID field 26b is associated with the value stored in the wafer ID field 25b of the changed-recipe etching result table 25a (described above in reference to FIG. 12) and the value stored in the wafer ID field 27b of the changed-recipe spectroscopic measurement data table 27a (described later).

The recipe change amount field 26c stores the amount of change from the standard recipe for each recipe parameter (for example, flow rate for each gas type) which is used to etch the wafer identified in the wafer ID field 26b. Although FIG. 13 shows gas flow rates in the recipe change amount field 26c as an example, the parameter stored in this field is not limited to gas flow rates but the field may store recipe data such as processing chamber internal pressure, processing time, and voltage applied to the electrodes 112a or 112b as well.

FIG. 14 shows a changed-recipe spectroscopic measurement data table 27a as an example of the changed-recipe spectroscopic measurement data storage area 27. The table includes a wafer ID field 27b, a wavelength field 27c, a time field 27d, and an emission intensity field 27e. This table is provided in the same number as the number of wafers for which spectroscopic measurement data has been obtained.

The wafer ID field 27b stores information which identifies the wafer 114. The value stored in the wafer ID field 27b is associated with the value stored in the wafer ID field 25b of the changed-recipe etching result data table 25a described above in reference to FIG. 12 and the value stored in the wafer ID field 26b of the changed-recipe recipe data table 26a described above in reference to FIG. 13.

The emission intensity field 27e stores measured emission intensity values at wavelengths in the wavelength field 27c and at times in the time field 27d.

The APC setup data candidate storage area 28 of the storage 22 shown in FIG. 1 stores information as candidates for APC setup data to be stored in the APC setup data storage area 15 of the storage 14 and information on results of estimation of candidates.

FIG. 15 shows an APC setup data candidate table 28a as an example of the APC setup data candidate storage area 28. The table includes an ID field 28b, an APC setup candidates field 281, and an evaluation result field 282. The APC setup candidates field 281 includes a monitor 1 field 281a, a monitor 2 field 281b, and a changed recipe parameter field 28g. The monitor 1 field 281a includes a wavelength 1 field 28c and a time interval 1 field 28d, and the monitor 2 field 281b includes a wavelength 2 field 28e and a time interval 2 field 28f. The evaluation result field 282 includes a fixed-recipe residual field 28h, a changed-recipe residual field 28i, a model difference field 28j, and an overall evaluation field 28k.

Information obtained by analysis processing which will be described later is stored in these fields.

The ID field 28b stores information which identifies the combination of data stored in the wavelength 1 field 28c, time interval 1 field 28d, wavelength 2 field 28e, time interval 2 field 28f, and changed-recipe parameter field 28g.

The wavelength 1 field 28c stores information which identifies the candidate for the wavelength to be used for APC. The value stored in row i of the wavelength 1 field (column) 28c is called WL1 for later explanation.

The time interval 1 field 28d stores information which identifies the candidate for the time interval to be used for APC. The information stored in the time interval 1 field 28d is associated with the information stored in the wavelength 1 field 28c. The value stored in row i of the time interval 1 field (column) 28d is called WLT1 for later explanation.

The wavelength 2 field 28e stores information which identifies the candidate for the wavelength to be used for APC. The value stored in row i of the wavelength 2 field (column) 28e is called WL2 for later explanation.

The time interval 2 field 28f stores information which identifies the candidate for the time interval to be used for APC. The information stored in the time interval 2 field 28f is associated with the information stored in the wavelength 2 field 28e. The value stored in row i of the time interval 2 field (column) 28f is called WLT2 for later explanation.

The changed-recipe parameter field 28g stores information which identifies the candidate for the recipe parameter to be used for APC. The value stored in row i of the changed-recipe parameter field (column) 28g is called Rcp for later explanation.

The values in each row represent a combination of APC setting values. In other words, using the values stored in the wavelength 1 field 28c, time interval 1 field 28d, wavelength 2 field 28e, and time interval 2 field 28f, the average emission intensity at wavelength WL1 in the wavelength field 24c of the spectroscopic measurement data table 24a shown in FIG. 11 at time interval WLT1 in the time interval field 24d is divided by the average emission intensity at wavelength WL2 in the wavelength field 24c at time interval WLT2 in the time interval field 24d and the result of the division (quotient) is defined as an emission intensity monitor value. Using this emission intensity monitor value, the recipe parameter specified by changed-recipe parameter Rcp stored in row i of the changed-recipe parameter field 28g is changed.

Similarly, the result of dividing the average emission intensity at wavelength WL1 in the wavelength field 27c of the spectroscopic measurement data table 27a shown in FIG. 14 at time interval WLT1 in the time interval field 27d by the average emission intensity at wavelength WL2 in the wavelength field 27c at time interval WLT2 in the time interval field 27d is also defined as an emission intensity monitor value.

The fixed-recipe residual field 28h stores information which identifies the degree of correlation between emission intensity monitor value and etching result for data with a fixed-recipe when the values stored in the wavelength 1 field 28c, time interval 1 field 28d, wavelength 2 field 28e, and time interval 2 field 28f, and the emission intensity monitor value calculated from the values in the spectroscopic measurement data table 24a shown in FIG. 11 are used. In this embodiment, the smaller the value is, the stronger the correlation is.

The changed-recipe residual field 28i stores information which identifies the degree of correlation between emission intensity monitor value and etching result for data with a changed recipe when the values stored in the wavelength 1 field 28c, time interval 1 field 28d, wavelength 2 field 28e, and time interval 2 field 28f, and the emission intensity monitor value calculated from the spectroscopic measurement data table 27a shown in FIG. 14 are used. In this embodiment, the smaller the value is, the stronger the correlation is.

The model difference field 28j stores information which identifies the magnitude of difference between the following two functions: the function representing the relation between emission intensity monitor value and etching result when the values stored in the wavelength 1 field 28c, time interval 1 field 28d, wavelength 2 field 28e, and time interval 2 field 28f and the emission intensity monitor value calculated from the spectroscopic measurement data table 24a shown in FIG. 11 are used, and the function representing the relation between emission intensity monitor value and etching result when the values stored in the wavelength 1 field 28c, time interval 1 field 28d, wavelength 2 field 28e, and time interval 2 field 28f and the emission intensity monitor value calculated from the spectroscopic measurement data table 27a shown in FIG. 14 are used. In this embodiment, the smaller the value is, the smaller the difference between the two functions is.

The overall evaluation field 28k stores information which indicates the degree of suitableness for APC of the combination of the wavelengths, time intervals, and recipe as stored in the wavelength 1 field 28c, time interval 1 field 28d, wavelength 2 field 28e, time interval 2 field 28f, and changed-recipe parameter field 28g. In this embodiment, the field stores the weighted sum of the values stored in the relevant row of the fixed-recipe residual field 28h, changed-recipe residual field 28i, and model difference field 28j. A combination for which the value in the overall evaluation field 28k is relatively small is presented to the apparatus manager and used for APC.

Analysis Processing by the Analysis Module 20

The analysis method according to this embodiment is an analysis method which determines the combination of wavelength, time interval, and recipe parameter for spectroscopic measurement data to be used for APC in the semiconductor etching process for etching a semiconductor wafer using plasma.

In the analysis method according to this embodiment, for each of candidates for the wavelength, time interval and recipe parameter to be used for APC, an evaluation is made of the degree of correlation between emission intensity monitor value and etching result with a fixed recipe, the degree of correlation between emission intensity monitor value and etching result with a changed recipe, and the difference between the correlation between emission intensity monitor value and etching result with a fixed recipe and the correlation between emission intensity monitor value and etching result with a changed recipe, and a suitable combination of wavelength, time interval, and recipe parameter for APC is determined.

This analysis method is used not only to determine the combination of wavelength, time interval and recipe but also can be used to determine the wavelength for use in APC, the time interval for use in APC, or the recipe for use in APC. For example, if one candidate is previously selected for any one factor (for example, time interval and recipe), the value of the other factor (for example, wavelength) for use in APC can be determined.

Next, how analysis processing according to this embodiment is performed will be described concretely.

In the production process, as a step prior to the step of sequentially etching wafers using the etching apparatus 1, the apparatus manager who operates the etching apparatus 1 carries out analysis using the analysis module 20 to determine the combination of wavelength, time interval, and recipe parameter to be used in APC.

Since the combination of wavelength, time interval, and recipe parameter which is suitable for APC varies depending on the structure of the surface film of the semiconductor wafer to be etched, it is necessary to carry out this analysis as appropriate at the start of etching. In the production process (mass production process), a plurality of wafers are sequentially etched by the etching apparatus 1 under the etching conditions determined by this analysis.

Figure 16:
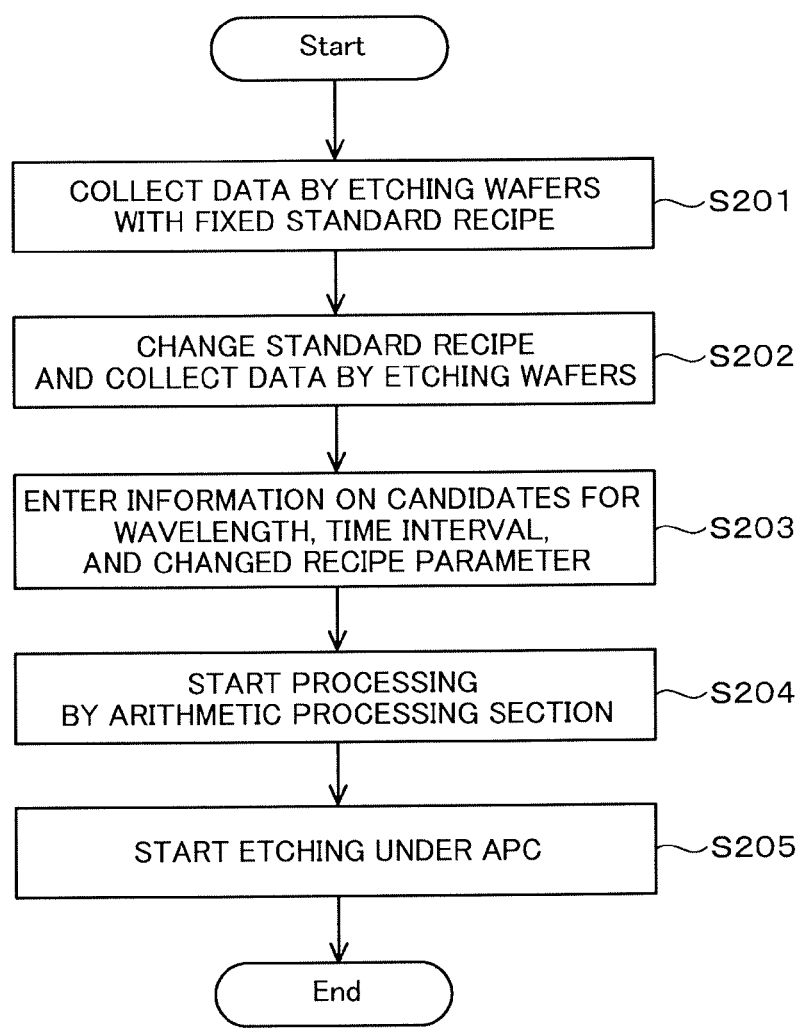
FIG. 16 is a flowchart showing the steps to be carried out by an apparatus manager according to an embodiment of the present invention.

FIG. 16 shows the steps which the apparatus manager carries out for analysis by the analysis module 20.

First, the apparatus manager collects spectroscopic measurement data and etching result data by etching a plurality of wafers sequentially with a fixed standard recipe (S201). Data is thus stored in the fixed-recipe etching result data table 23a shown in FIG. 10 and the fixed-recipe spectroscopic measurement data table 24a shown in FIG. 11.

Next, the apparatus manager changes the recipe and collects spectroscopic measurement data and etching result data by etching a plurality of wafers sequentially (S202). For example, the flow rate of the gas type specified by the apparatus manager is changed. The amount of change may be specified by the apparatus manager or the gas flow rate may be automatically changed by a predetermined amount. In this embodiment, it is assumed that only one recipe parameter is changed at a time from the standard recipe. However, data may be collected by changing two or more recipe parameters. Furthermore, the recipe may be changed for a specific part of the etching time: for example, the gas flow rate in the latter half of the etching time may be changed. Consequently, data is stored in the changed-recipe etching result data table 25a shown in FIG. 12, the changed-recipe recipe data table 26a shown in FIG. 13, and the changed-recipe spectroscopic measurement data table 27a shown in FIG. 14.

Figure 23:
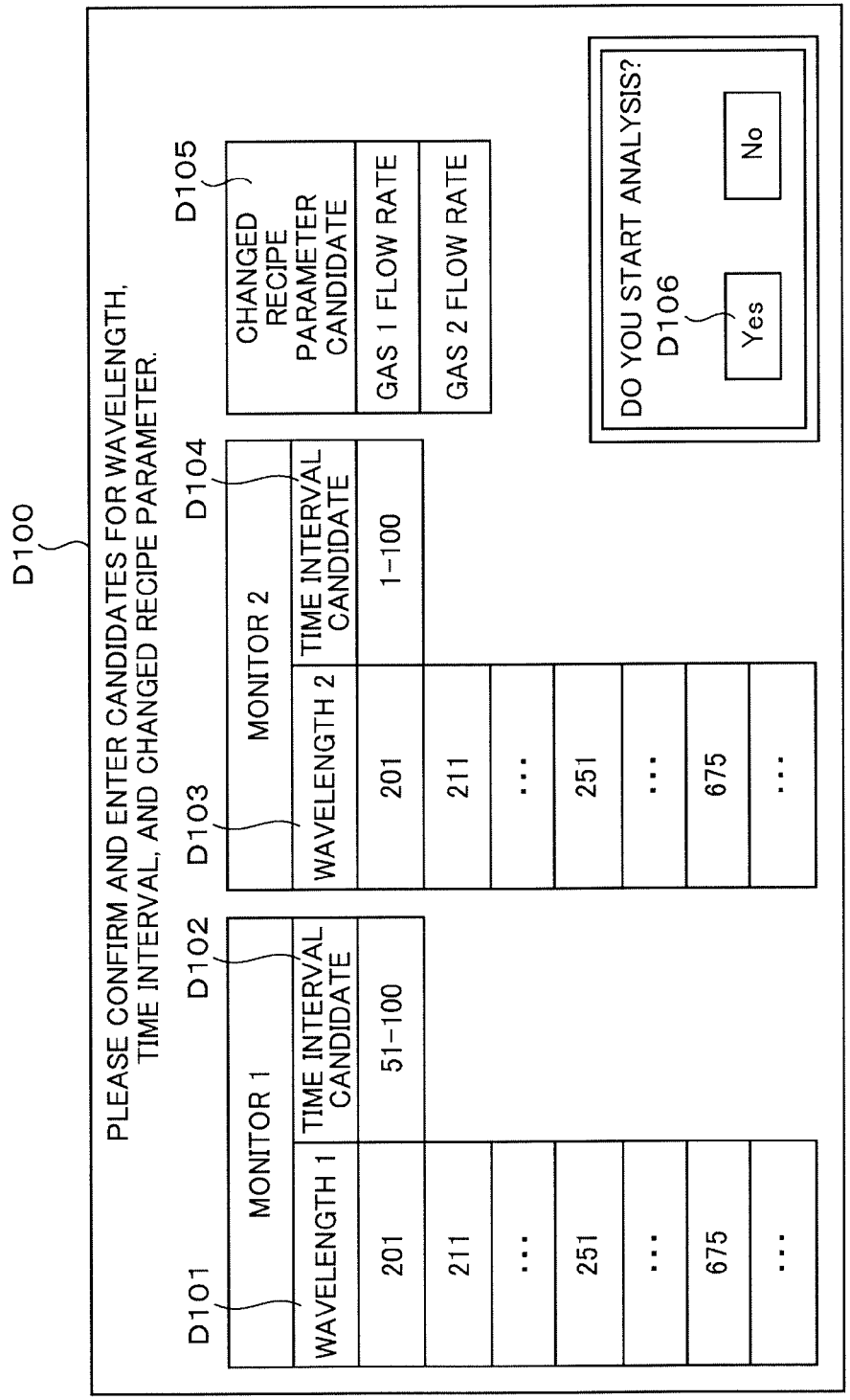
FIG. 23 is a front view of the input display screen for analysis processing according to an embodiment of the present invention.

Next, the apparatus manager enters candidates for wavelength, time interval, and changed recipe parameter on an input display screen shown in FIG. 23 (S203) and starts analysis processing (S204).

As wavelength candidates, wavelengths within a specific numerical range such as 201 nm and 211 nm, the emission wavelength of an element related to the etching process, such as 251 nm (emission wavelength of Si), and 675 nm (emission wavelength of Ar) may be entered. As a time interval candidate, etching time information such as a time interval (51-100) in the latter half of the etching time or the entire etching time (1-100) is entered. As a changed recipe parameter candidate, information on the changed recipe parameter used in the etching process at S202 is entered.

The apparatus manager gives a command to perform analysis processing and the analysis module 20 performs analysis processing. The apparatus manager enters settings for APC using the result of analysis by the analysis module 20 to perform etching (S205).

Figure 17:
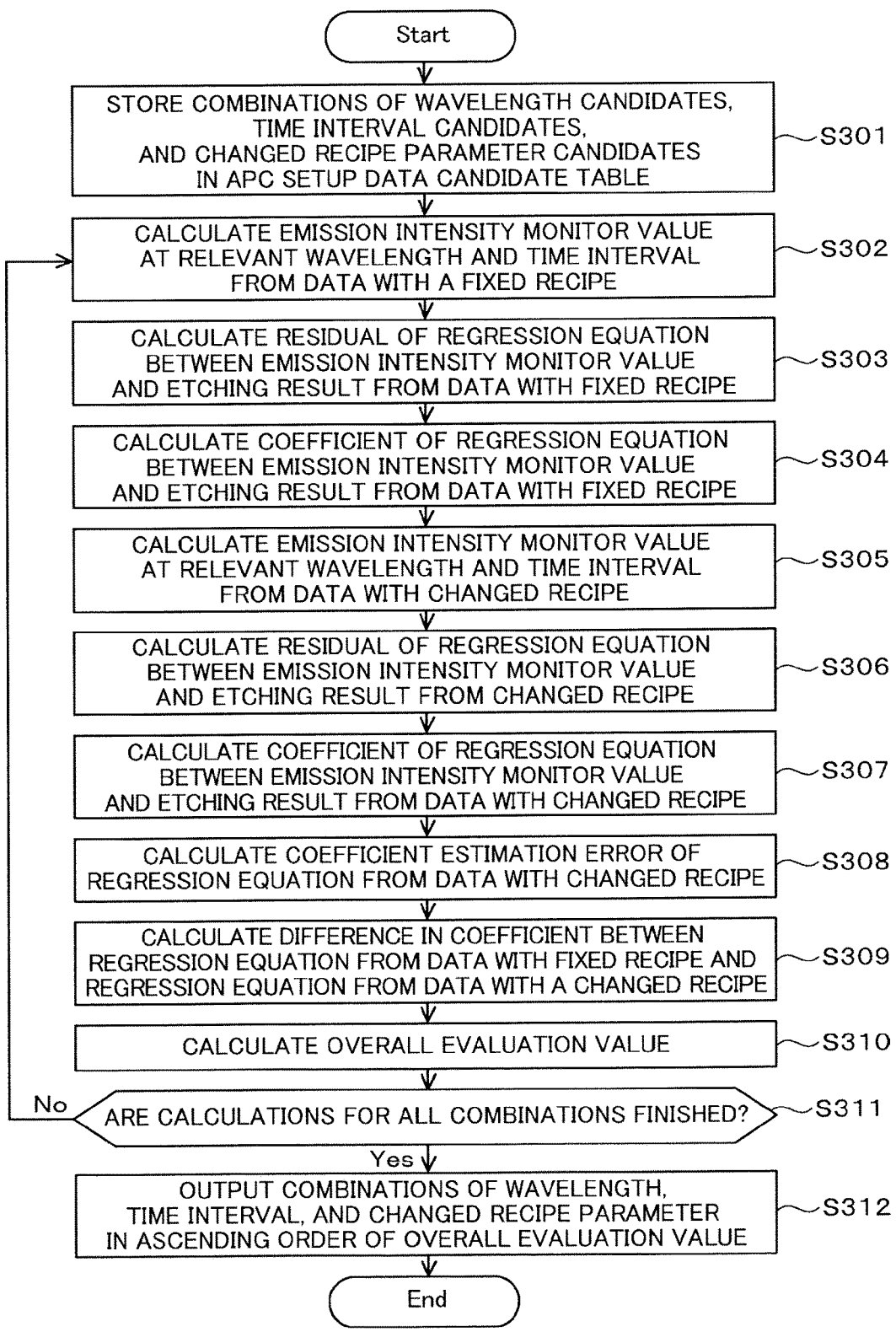
FIG. 17 is a flowchart showing analysis steps to be taken in an arithmetic processing section according to an embodiment of the present invention.

Next, the flow of analysis processing steps which are performed by the analysis module 20 will be described referring to FIG. 17.

When a button D106 to start analysis processing is clicked with a cursor (not shown) on a display D100 shown in FIG. 23, the analysis module 20 starts analysis processing. First, combinations of wavelength candidates D101 and D103, time interval candidates D102 and D104, and changed recipe candidate D105 are created from the information on wavelength candidates, time interval candidates and changed recipe candidates as entered on the display D100, and stored in the APC setup data candidate table 28a shown in FIG. 15 (S301). Next, using the information on the wavelength candidates D101 and D103 and time interval candidates D102 and D104 in the combinations of wavelength candidates D101 and D103, time interval candidates D102 and D104, and changed recipe candidate D105 as created at S301, the emission intensity monitor value is calculated from data with a fixed recipe (S302). Also, as information indicating the degree of correlation between emission intensity and etching result with a fixed recipe, the residual of the regression equation (regression line) between emission intensity monitor value and etching result is calculated (S303). Furthermore, the coefficient of the regression equation (regression line) between emission intensity monitor value and etching result is calculated (S304).

Next, using data obtained by changing the changed-recipe parameter candidate D105 in the combination of wavelength, time interval, and changed recipe parameter as created at S301, the emission intensity monitor value with the changed recipe at the wavelength and time interval in this combination is calculated (S305). As information indicating the degree of correlation between the calculated emission intensity monitor value and the etching result with the changed recipe, the residual of the regression equation (regression line) between emission intensity monitor value and etching result is calculated (S306). Furthermore, the coefficient of the regression equation (regression line) between emission intensity monitor value and etching result is calculated (S307) and the estimation error of the coefficient of the regression equation (regression line) is calculated (308).

From the coefficients of the regression equations (regression lines) and coefficient estimation error as calculated at S304, S307, and S308, the difference between the coefficients of the regression equations is calculated as the information indicating the difference between the correlation of emission intensity monitor value and etching result with a fixed recipe and the correlation of emission intensity monitor value and etching result with a changed recipe (S309).

The overall evaluation value 28k which indicates the degree of suitableness for APC of a combination of wavelength, time interval, and changed recipe parameter is calculated from the residuals of the regression equations (regression lines) as calculated at S303 and S306 and the difference between the coefficients of the regression equations (equation lines) as calculated at S309 (S310). The steps from S302 to S310 are carried out for all the combinations of wavelength candidates D101, D103, time interval candidates D102, D104, and changed recipe parameter candidate D105 and when all calculations are finished (Yes at S311), a combination of wavelength, time interval, and changed recipe parameter for which the overall evaluation value 28k is small is presented to the apparatus manager as the wavelength, time interval, and changed recipe parameter to be used for APC (S312).

Next, the above steps will be described in detail. (S301): The arithmetic processing section 21 creates a plurality of combinations of two wavelengths, two time intervals, and a changed recipe parameter, using the wavelength candidates and time interval candidate entered in the wavelength 1 input field D101 and time interval 1 input field D102 of the display D100 shown in FIG. 23, the wavelength candidates and time interval candidate entered in the wavelength 2 input field D103 and time interval 2 input field D104, and the changed recipe parameter candidate entered in the changed recipe parameter input field D105, and stores each combination of wavelengths, time intervals and changed recipe parameter in the wavelength 1 field 28c, time interval 1 field 28d, wavelength 2 field 28e, time interval 2 field 28f, and changed recipe parameter field 28g of the APC setup data candidate table 28a shown in FIG. 15, respectively. The combinations stored there may be combinations of all wavelengths, time intervals, and changed recipe parameters entered in the input fields D101, D102, D103, D104, and D105. Also, the arithmetic processing section 21 assigns numbers to the first and subsequent rows in the ID field 28b sequentially.

The arithmetic processing section 21 performs steps S302 to S310 for the combination of wavelengths, time intervals, and changed recipe parameter which is stored in each row of the APC setup data candidate table 28a. Hereinafter, the row for which processing is performed will be called "the row concerned".

(S302): The arithmetic processing section 21 creates an emission intensity monitor value data table 29a which includes the wafer ID field 29b, emission intensity monitor value field 29c, and etching result field 29d, as shown in FIG. 18.

The wafer ID field 29b of the emission intensity monitor value data table 29a stores information which indicates the wafer for which data has been acquired, for example, information stored in the wafer ID field 23b of the fixed-recipe etching result data table 23a shown in FIG. 10.

The emission intensity monitor value field 29c stores the emission intensity monitor value as the first average emission intensity value (described below) divided by the second average emission intensity value (described below). The first average emission intensity value is the average of values stored in the column identified by the wavelength stored in the row concerned of the wavelength 1 field 28c of the APC setup data candidate table 28a shown in FIG. 15 and in the time row identified by the time interval 1 field 28d, in the emission intensity value field 24e of the fixed-recipe spectroscopic measurement data table 24a shown in FIG. 11. The second average emission intensity value is the average of values stored in the column identified by the wavelength stored in the row concerned of the wavelength 2 field 28e of the APC setup data candidate table 28a and in the time row identified by the time interval 2 field 28f, in the emission intensity value field 24e of the fixed-recipe spectroscopic measurement data table 24a.

The etching result field 29d of the emission intensity monitor value data table 29a shown in FIG. 18 stores information stored in the etching result field 23c of the fixed-recipe etching result data table 23a.

(S303): The arithmetic processing section 21 calculates the square average (AveSe$_1$) of the residual of the regression equation as information which indicates the degree of correlation between emission intensity monitor value and etching result for data with a fixed recipe, using the data stored in the emission intensity monitor value data table 29a and the following equations (Equation 1) to (Equation 5).

$$X_{11} = \Sigma x_i^2 - \frac{(\Sigma x_i)^2}{n} \quad \text{(Equation 1)}$$

$$X_{12} = \Sigma y_i^2 - \frac{(\Sigma y_i)^2}{n} \quad \text{(Equation 2)}$$

$$X_{13} = \Sigma x_i y_i - \frac{(\Sigma x_i)(\Sigma y_i)}{n} \quad \text{(Equation 3)}$$

$$a_1 = \frac{X_{13}}{X_{11}} \quad \text{(Equation 4)}$$

$$AveSe_1 = \frac{(X_{12} - a_1 X_{13})}{n} \quad \text{(Equation 5)}$$

In the above equations, $x_i$ denotes the value stored in the i-th column of the emission intensity monitor value field 29c of the emission intensity monitor value data table 29a shown in FIG. 18; $y_i$ denotes the value stored in the i-th column of the emission intensity monitor value field 29c; n denotes the number of columns of the emission intensity monitor value data table 29a; and E denotes the sum of values in all the columns of the emission intensity monitor value data table 29a.

The meanings of the calculated values are explained below referring to FIG. 20. The graph of FIG. 20 is a scatter diagram which plots the values stored in the emission intensity monitor value field 29c and the values stored in the etching result field 29d for each wafer ID 29b in the emission intensity monitor value data table 29a shown in FIG. 18.

Figure 20:
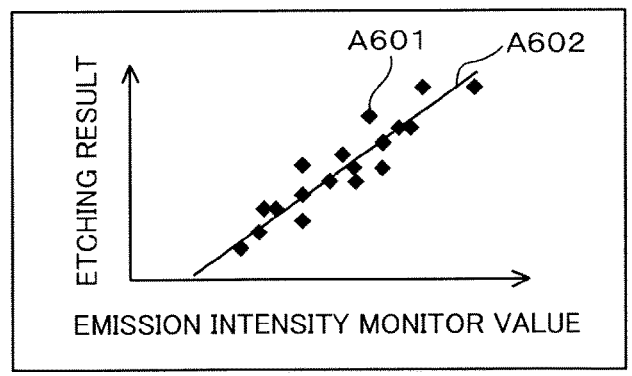
FIG. 20 is a scatter diagram showing an example of the regression equation between emission intensity monitor value and etching result.

In FIG. 20, points such as A601, which represent the values stored in the columns of the emission intensity monitor value field 29c of the emission intensity monitor value data table 29a, are plotted with the values stored in the emission intensity monitor value field 29c on the horizontal axis and the values stored in the etching result field 29d on the vertical axis.

The value ($X_{11}$) calculated by (Equation 1) represents dispersion of plotted points in FIG. 20 in the horizontal axis direction (emission intensity monitor value) and the value ($X_{12}$) calculated by (Equation 2) represents dispersion of plotted points in FIG. 20 in the horizontal axis direction (etching result). The value ($X_{13}$) calculated by (Equation 3) represents the sum of products of deviation of plotted points in FIG. 20 in the horizontal axis direction and vertical axis direction, in which when the value of a plotted point in the vertical axis direction is larger, its value in the horizontal axis direction is also larger.

In FIG. 20, line A602 represents a line (regression equation) in which the average square sum of distances from points is minimum. The first residual square average ($AveSe_1$) calculated by (Equation 5) represents the square average of distances (residuals) between points and the line.

As for data with a fixed recipe, when the correlation between emission intensity monitor value and etching result is stronger, the residual square average ($AveSe_1$) is smaller. The first residual square average ($AveSe_1$) calculated by (Equation 5) is stored in the row concerned of the fixed-recipe residual field 28h of the APC setup data candidate table 28a shown in FIG. 15 as information for evaluation of the combination of wavelengths and time intervals in the row concerned.

Alternatively, a value other than the residual square average thus calculated may be used, provided that it indicates the degree of correlation between emission intensity monitor value and etching result. For example, it may be the reciprocal of the absolute value of the coefficient of correlation between emission intensity monitor value and etching result or the reciprocal of the square of the coefficient of correlation.

(S304): The arithmetic processing section 21 calculates the gradient of the regression equation (regression line) between emission intensity monitor value and etching result for data with a fixed recipe as information which indicates the direction of correlation between emission intensity monitor value and etching result.

The arithmetic processing section 21 calculates variable ($a_1$) on the left-hand side of (Equation 4), using (Equation 1), (Equation 3), and (Equation 4) and the values stored in the emission intensity monitor field 29c and etching result field 29d of the emission intensity monitor value data table 29a shown in FIG. 18. This variable ($a_1$) represents the gradient of line A602 in FIG. 20. The arithmetic processing section 21 uses the calculated gradient ($a_1$) at the step S310 which will be described later.

(S305): The arithmetic processing section 21 creates a data table corresponding to the emission intensity monitor value data table 29a shown in FIG. 18, using data with a changed recipe. As an example, FIG. 19 shows an emission intensity monitor value data table 29-2a in which data with a changed recipe is used.

Let's assume that Rcp denotes the value stored in the row concerned with the changed recipe parameter field 28g of the APC setup data candidate table 28a shown in FIG. 15. The emission intensity monitor data table 29-2a shown in FIG. 19 stores the data on the wafer for which the recipe parameter identified by Rcp has been changed, among the wafers for which the etching result and spectroscopic measurement data have been obtained.

For example, the wafer ID field 29-2b stores, as information indicating the wafer for which data has been obtained, a wafer ID among wafer IDs stored in the wafer ID field 23b of the changed-recipe etching result data table 23a shown in FIG. 10, for which the value of the recipe parameter corresponding to Rcp in the recipe change amount field 26c of the changed-recipe recipe data table 26a shown in FIG. 13 is not 0.

The emission intensity monitor value field 29-2c stores an emission intensity monitor value as the third average emission intensity value (described below) divided by the fourth average emission intensity value (described below). The third average emission intensity value is the average of values stored in the column identified by the wavelength stored in the row concerned with the wavelength 1 field 28c of the APC setup data candidate table 28a shown in FIG. 15 and in the time row identified by the time interval 1 field 28d, in the emission intensity value field 27e of the changed-recipe spectroscopic measurement data table 27a shown in FIG. 14. The fourth average emission intensity value is the average of values stored in the column identified by the wavelength stored in the row concerned with the wavelength 2 field 28e of the APC setup data candidate table 28a and in the time row identified by the time interval 2 field 28f, in the emission intensity value field 27e of the changed-recipe spectroscopic measurement data table 27a. Among these averages, the value of the wafer for which the recipe parameter identified by Rcp has been changed is stored here.

The etching result field 29-2d of the emission intensity monitor value data table 29-2a stores the value of the wafer for which the value of the recipe parameter corresponding to Rcp in the recipe change amount field 26c shown in FIG. 13 is not 0, among the data stored in the etching result field 25c of the changed-recipe etching result table 25a shown in FIG. 12.

(S306): The arithmetic processing section 21 calculates the residual square average ($AveSe_2$) of the regression equation as information which indicates the degree of correlation between emission intensity monitor value and etching result for data with a fixed recipe, using the following equations, (Equation 6) to (Equation 10), which are obtained by substituting the data stored in the emission intensity monitor value data table 29a-2a shown in FIG. 19 in (Equation 1) to (Equation 5).

$$X'_{11} = \Sigma x'^2_i - \frac{(\Sigma x'_i)^2}{n'} \quad \text{(Equation 6)}$$

$$X'_{12} = \Sigma y'^2_i - \frac{(\Sigma y'_i)^2}{n'} \quad \text{(Equation 7)}$$

$$X'_{13} = \Sigma x'_i y'_i - \frac{(\Sigma x'_i)(\Sigma y'_i)}{n'} \quad \text{(Equation 8)}$$

$$a_2 = \frac{X'_{13}}{X'_{11}} \quad \text{(Equation 9)}$$

$$AveSe_2 = \frac{(X'_{12} - a_2 X'_{13})}{n'} \quad \text{(Equation 10)}$$

In the above equations, $x'_i$ denotes the value stored in the i-th column of the emission intensity monitor value field 29-2c of the emission intensity monitor value data table 29-2a shown in FIG. 19; $y'_i$ denotes the value stored in the i-th column of the emission intensity monitor value field 29-2c; n' denotes the number of columns of the emission intensity monitor value data table 29-2a; and Σ denotes the sum of values in all the columns of the emission intensity monitor value data table 29-2a.

The second residual square average ($AveSe_2$) calculated by (Equation 10) represents the square average of distances (residuals) between the line and the regression equation as in the case of (Equation 5).

As for data with a changed recipe, when the correlation between emission intensity monitor value and etching result is stronger, the second residual square average (AveSe$_2$) is smaller. The second residual square average (AveSe$_2$) calculated here is stored in the row concerned of the changed-recipe residual field 28i of the APC setup data candidate table 28a shown in FIG. 15 as information for evaluation of the combination of wavelengths and time intervals in the row concerned.

Alternatively, a value other than the residual square average thus calculated may be used, provided that it indicates the degree of correlation between emission intensity monitor value and etching result. For example, it may be the reciprocal of the absolute value of the coefficient of correlation between emission intensity monitor value and etching result or the reciprocal of the square of the coefficient of correlation.

(S307): The arithmetic processing section 21 calculates the gradient of the regression equation (regression line) between emission intensity monitor value and etching result for data with a changed recipe as information which indicates the direction of correlation between emission intensity monitor value and etching result.

The arithmetic processing section 21 calculates variable (a$_2$) on the left-hand side of (Equation 9), using (Equation 6), (Equation 8), and (Equation 9) and the values stored in the emission intensity monitor field 29-2c and etching result field 29-2d of the emission intensity monitor value data table 29-2a shown in FIG. 19. This variable (a$_2$) represents the gradient of the regression equation (regression line) created from data with a changed recipe.

(S308): The arithmetic processing section 21 calculates information which indicates a gradient estimation error of the regression equation (regression line) obtained from data with a changed recipe, using the following equation (Equation 11):

$$\Delta a_2 = \frac{AveSe_2}{X'_{11}} \qquad \text{(Equation 11)}$$

The meaning of the calculated value is explained below referring to FIGS. 21A and 21B. The graphs of FIGS. 21A and 21B are scatter diagrams which plot the values stored in the emission intensity monitor value field 29-2c and the values stored in the etching result field 29-2d for each wafer ID 29-2b in the emission intensity monitor value data table 29-2a shown in FIG. 19.

Figure 21A:
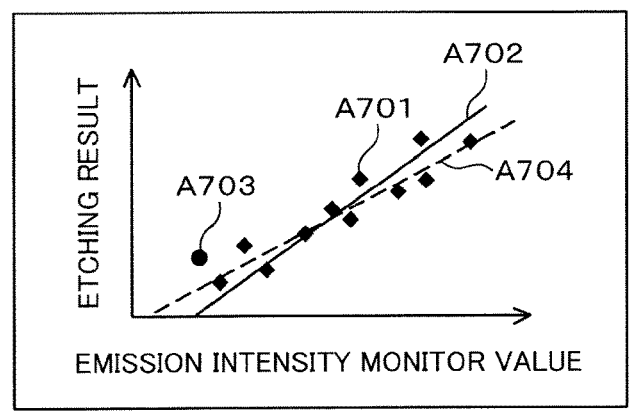
FIG. 21A is a scatter diagram showing an example that the coefficient of the regression equation provides a high estimation accuracy.
Figure 21B:
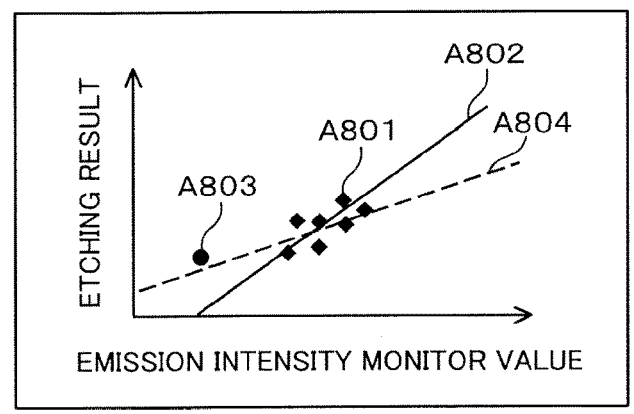
FIG. 21B is a scatter diagram showing an example that the coefficient of the regression equation provides a low estimation accuracy.

In FIGS. 21A and 21B, points such as A701 and A801, which represent the values stored in the columns of the emission intensity monitor value field 29-2c of the emission intensity monitor value data table 29-2a shown in FIG. 19, are plotted with the values stored in the emission intensity monitor value field 29-2c on the horizontal axis and the values stored in the etching result field 29-2d on the vertical axis. Lines A702 and A802 represent lines (regression equations) in which the average square sum of distances from points is minimum. Points A703 and A803 represent data missing from the emission intensity monitor value data table 29-2a (due to a failure in data transfer from the inspection device, etc.) and lines A704 and A804 represent regression equations obtained by adding points A703 and A803 to points A701 and A801.

It is known that line A704 is smaller in change (change in gradient) from the original line A702 than line A804. Dispersion (X$_{11}$) in the horizontal axis direction is larger in the scatter diagram of FIG. 21A than in the scatter diagram of FIG. 21B and in the case shown in FIG. 21A, gradient estimation can be less affected by missing data, etc. Regarding the gradient estimation error ($\Delta a_2$) calculated by (Equation 11), when dispersion (X'$_{11}$) in the horizontal axis direction is larger, the gradient estimation error is smaller.

(S309): The arithmetic processing section 21 calculates the value of evaluation of the difference between the direction of correlation with a fixed recipe and the direction of correlation with a changed recipe from the following (Equation 12), using the variables (a$_1$) and (a$_2$) calculated by (Equation 4) and (Equation 9) and the variable ($\Delta a_2$) indicating the gradient estimation error calculated by (Equation 11).

$$E_a\{|a_1-a_2|+\Delta a_2\}^2 \times \Delta ei^2 \qquad \text{(Equation 12)}$$

(Equation 12) suggests that when the difference between the gradient of the regression equation with a fixed recipe and the gradient of the regression equation with a changed recipe is larger or the gradient estimation error is larger, the value (E$_a$) of evaluation of gradient difference on the left-hand side is larger. $\Delta ei$ on the right-hand side represents the difference between the emission intensity monitor value control target eit and the minimum emission intensity monitor value eimin with a fixed recipe as shown in FIG. 22A. The equation suggests that when the difference from the control target is larger, the amount of recipe change is larger and the contribution of gradient difference is larger.

As for data with a fixed recipe as well, the gradient estimation error of the regression equation may be calculated and added to the inside of the parentheses of (Equation 12). Also, $\Delta a2$ may be multiplied by a constant factor (1.5, 2 and so on). (X$_{11}$), which indicates dispersion of emission intensity monitor values with a fixed recipe, may be used instead of $\Delta ei^2$.

The arithmetic processing section 21 stores the value (E$_a$) of evaluation of gradient difference as calculated by (Equation 12) in the row concerned with the model difference field 28j of the APC setup data candidate table 28a.

(S310): The arithmetic processing section 21 calculates the degree of suitableness for APC of a combination of wavelength, time interval, and changed recipe parameter, using the following equation (Equation 13):

$$E_{all} = AveSe_1 \times \alpha_1 AveSe_2 \times \alpha_2 + E_a \times \alpha_3 \qquad \text{(Equation 13)}$$

On the right-hand side of (Equation 13), the first term is a term for evaluating the degree of correlation with a fixed recipe, the second term is a term for evaluating the degree of correlation with a changed recipe, and the third term is a term for evaluating the difference in correlation tendency between a fixed recipe and a changed recipe. Coefficients $\alpha_1$, $\alpha_2$, and $\alpha_3$ are weighting factors of the terms which are determined by the apparatus manager, etc. (Equation 13) suggests that when the evaluation value (E$_{all}$) calculated by (Equation 13) for a combination of wavelength, time interval, and recipe is small, it is a combination which ensures that the correlation is strong with a fixed recipe and with a changed recipe and the direction of correlation with a fixed recipe is the same as with a changed recipe.

The arithmetic processing section 21 stores the calculated evaluation value (E$_{all}$) in the row concerned with the overall evaluation field 28k of the APC setup data candidate table 28a shown in FIG. 15.

(S311): If the arithmetic processing section 21 has finished calculating overall evaluation values (E$_{all}$) for all combinations of wavelength, time interval, and changed recipe parameter, it proceeds to step S312 or if it has not finished, it returns to step S302 and performs processing for the next combination of wavelength, time interval and changed recipe parameter.

Figure 24:
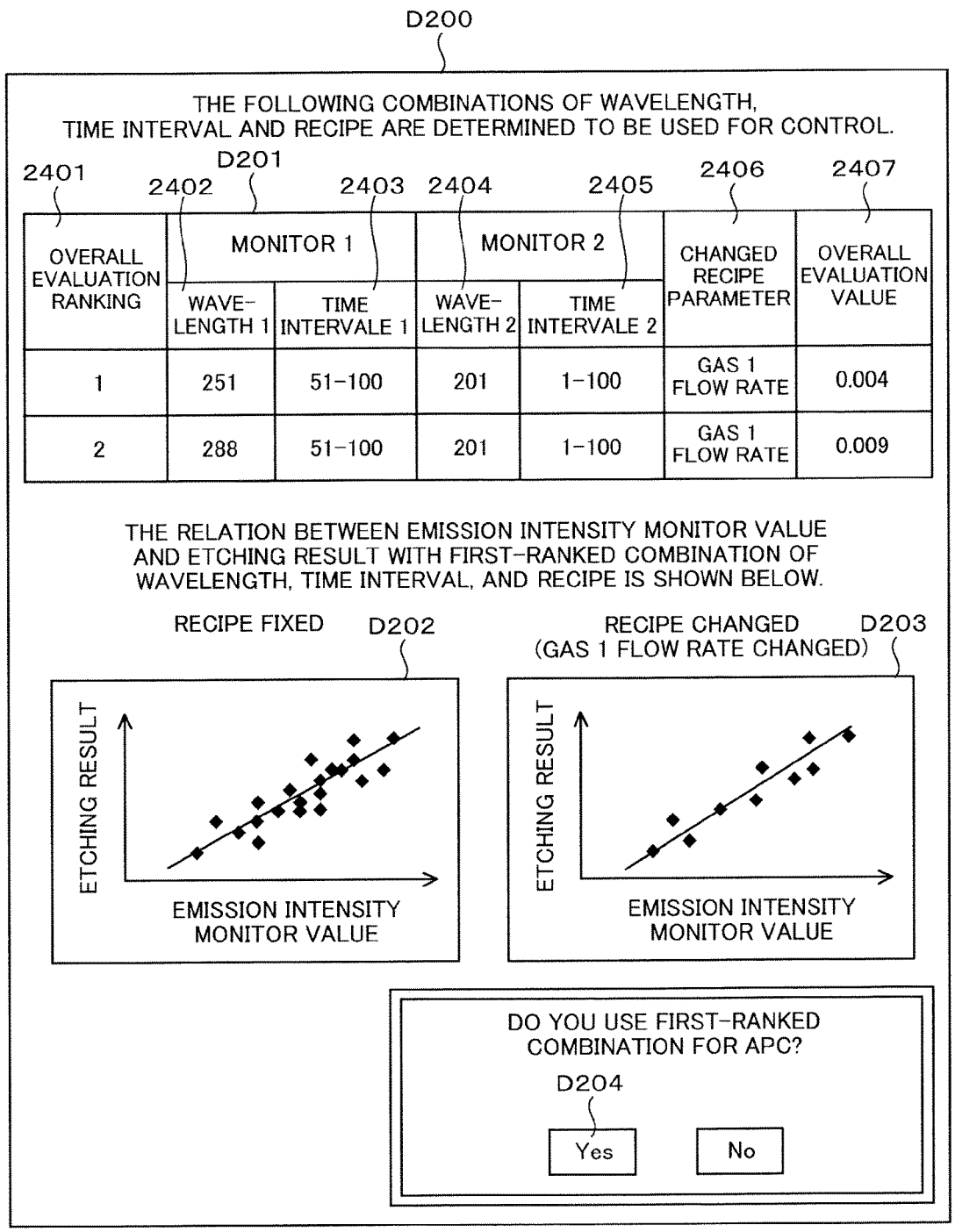
FIG. 24 is a front view of the display screen which shows analysis results according to an embodiment of the present invention.

(S312): The arithmetic processing section 21 outputs the result of analysis processing on the display, specifically the values stored in the APC setup data candidate table 28a shown in FIG. 15 and data related to scatter diagrams, and ends the processing sequence. FIG. 24 shows an example of the output display screen of the output module 31 which is presented to the operator by the arithmetic processing section 21.

The output display screen D200 shown in FIG. 24 includes a table D201 which lists the values stored in the rows of the wavelength 1 field 28c, time interval 1 field 28d, wavelength 2 field 28e, time interval 2 field 28f, changed recipe parameter field 28g, and overall evaluation field 28k, in the ascending order of the value stored in the overall evaluation field 28k of the APC setup data candidate table 28a shown in FIG. 15.

As for the combination of wavelengths, time intervals and changed recipe parameter for which the value in the overall evaluation field 28k is the smallest, D202 is a scatter diagram of emission intensity monitor value and etching result with a fixed recipe as obtained by calculation of emission intensity monitor values using the relevant wavelengths and time intervals. Similarly, D203 is a scatter diagram of emission intensity monitor value and etching result for data with a changed recipe in which the value of the relevant changed recipe parameter is changed.

The apparatus manager can know the combination of wavelengths, time intervals and changed recipe parameter to be used for APC by checking the output display screen D200 shown in FIG. 24.

The combination of wavelengths 2402, 2404, time intervals 2403, 2405, and changed recipe parameter 2406 which corresponds to the smallest value of overall evaluation 2407 and the first place of overall evaluation ranking 2401 in the table D201 shown in FIG. 24 is stored in the columns of the APC setup data candidate table 15a shown in FIG. 4. As the apparatus manager clicks the button D204 for execution of APC with the cursor (not shown) on the display screen D200 to acknowledge execution of APC with the first-ranked combination, the control section 13 of the etching module 10 controls the plasma processing section 11 using the data stored in the APC setup data table 15a so that the wafers 114 are etched sequentially.

As explained so far, the combination of wavelengths, time intervals and changed recipe parameter to be used for APC can be selected among many combinations of wavelengths, time intervals and changed recipe parameter, using the analysis method which is performed by the etching apparatus 1 (analysis module 20) according to this embodiment.

According to this embodiment, the wavelengths and time intervals for calculation of emission intensity monitor values can be appropriately determined from spectroscopic measurement data. Also, the recipe parameter to be changed for APC can be appropriately determined among a plurality of recipe parameters. Consequently, even when the recipe is changed, the correlation between emission intensity monitor value and etching result is stabilized with a constant tendency and the etching result is controlled with high accuracy.

The invention has been so far explained in reference to the preferred embodiment thereof.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

What is claimed is:

1. A plasma processing apparatus which performs plasma processing on a specimen with Advanced Process Control (APC) in use as control to suppress fluctuations in plasma processing by feedback control or feedforward control, the apparatus comprising:
   an analysis unit configured to select a combination for the APC of plasma emission wavelength, time interval for the plasma emission wavelength, and a parameter for the plasma processing,
   wherein the analysis unit is configured to
      obtain a first regression equation representing correlation between a plasma emission intensity and a plasma processing result from temporal change data of the plasma processing;
      change said parameter for the plasma processing by employing the plasma emission intensity and the plasma processing result so as to obtain a second regression equation representing correlation between the plasma emission intensity and the plasma processing result according to a changed recipe based on experimental data; and
      select a combination of the plasma emission wavelength, the time interval for the plasma emission wavelength, and said parameter for the plasma processing based on a difference between a gradient of the first regression equation for the fixed recipe and a gradient of the second regression equation, and
   wherein the analysis unit further calculates a weighted sum of a residual of the first regression equation and a residual of the second regression equation and finds the combination based on the difference and the weighted sum.

2. The plasma processing apparatus according to claim 1, wherein the parameter is provided in plurality.

3. A plasma processing apparatus which performs plasma processing on a specimen with Advanced Process Control (APC) in use as control to suppress fluctuations in plasma processing by feedback control or feedforward control, and is connected to an analysis unit configured to select a combination for the APC of emission wavelength, time interval for the emission wavelength, and a parameter for the plasma processing,
   an etching unit connected to an analysis unit configured to find a combination for the APC of plasma emission wavelength, time interval for the plasma emission wavelength, and a parameter for the plasma processing,
   wherein the analysis unit is further configured to
      obtain a first regression equation representing correlation between a plasma emission intensity and a plasma processing result from temporal change data of the plasma processing;
      change said parameter for the plasma processing by employing the plasma emission intensity and the plasma processing result, so as to obtain a second regression equation representing correlation between the plasma emission intensity and plasma processing result; and
      select a combination of the plasma emission wavelength, the time interval for the plasma emission wavelength, and said parameter for the plasma processing based on a difference between a gradient of the first regression equation and a gradient of the second regression, and wherein the analysis unit further calculates a weighted sum of a residual of the first regression equation and a residual of the second regression equation and finds the combination based on the difference and the weighted sum.

4. The plasma processing apparatus according to claim 3, wherein the parameter is provided in plurality.

5. A plasma processing apparatus which performs plasma processing on a specimen with Advanced Process Control (APC) in use as control to suppress fluctuations in plasma processing by feedback control or feedforward control, the apparatus comprising:

an analysis unit configured to select a combination for the APC of plasma emission wavelength, time interval for the plasma emission wavelength, and a parameter for the plasma processing, wherein the analysis unit is configured to obtain a first regression equation representing correlation between a plasma emission intensity and a plasma processing result from temporal change data of the plasma processing;

change said parameter for the plasma processing by employing the plasma emission intensity and the plasma processing result so as to obtain a second regression equation representing correlation between the plasma emission intensity and the plasma processing result according to a changed recipe based on experimental data; and select a combination of the plasma emission wavelength, the time interval for the plasma emission wavelength, and said parameter for the plasma processing based on a difference between a gradient of the first regression equation for the fixed recipe and a gradient of the second regression equation, wherein the analysis unit adds to the difference estimation error of the second regression equation as a square average of residual of the second regression equation divided by the emission intensity result by changing the parameter, and finds the combination based on the difference to which the estimation error is added.

6. A plasma processing apparatus which performs plasma processing on a specimen with Advanced Process Control (APC) in use as control to suppress fluctuations in plasma processing by feedback control or feedforward control, and is connected to an analysis unit configured to select a combination for the APC of plasma emission wavelength, time interval for the plasma emission wavelength, and a parameter for the plasma processing, wherein the analysis unit is further configured to obtain a first regression equation representing correlation between a plasma emission intensity and a plasma processing result from temporal change data of the plasma processing;

change said parameter for the plasma processing by employing the plasma emission intensity and the plasma processing result, so as to obtain a second regression equation representing correlation between the plasma emission intensity and plasma processing result; and select a combination of the plasma emission wavelength, the time interval for the plasma emission wavelength, and said parameter for the plasma processing based on a difference between a gradient of the first regression equation and a gradient of the second regression, wherein the analysis unit adds to the difference estimation error of the second regression equation as a square average of residual of the second regression equation divided by the plasma emission intensity result by changing the parameter, and finds the combination based on the difference to which the estimation error is added.

* * * * *